United States Patent [19]

Heinemann et al.

[11] Patent Number: 5,250,533
[45] Date of Patent: Oct. 5, 1993

[54] FUNGICIDAL PYRIDINYLPYRIMIDINES

[75] Inventors: Ulrich Heinemann, Leichlingen; Alexander Klausener, Krefeld; Dieter Berg, Wuppertal; Stefan Dutzmann, Duesseldorf; Wilhelm Brandes, Leichlingen, all of Fed. Rep. of Germany

[73] Assignee: Bayer Aktiengesellschaft, Leverkusen, Fed. Rep. of Germany

[21] Appl. No.: 844,808

[22] Filed: Mar. 2, 1992

Related U.S. Application Data

[63] Continuation-in-part of Ser. No. 608,100, Oct. 31, 1990, abandoned.

[30] Foreign Application Priority Data

Jul. 12, 1989 [DE] Fed. Rep. of Germany ....... 3940476

[51] Int. Cl.$^5$ .................. A01N 43/54; C07D 401/04; C07D 401/14
[52] U.S. Cl. ..................................... 514/256; 544/60; 544/61; 544/58.6; 544/121; 544/122; 544/123; 544/80; 544/82; 544/295; 544/333; 544/319; 544/327; 544/328; 514/269; 514/227.8; 514/228.2; 514/232.2; 514/232.5; 514/235.2; 514/235.8
[58] Field of Search ................ 514/256, 269; 544/319, 544/328, 327, 333, 60, 61, 58.6, 121, 122, 123, 80, 82, 295

[56] References Cited

FOREIGN PATENT DOCUMENTS 0259139 3/1988 European Pat. Off. .
0270362 6/1988 European Pat. Off. .

OTHER PUBLICATIONS

J. J. Lafferty and F. H. Case, "The Preparation and Properties of Certain Pyridylpyrimidines and Bidiazines . . . ," J. Org. Chem, 32 (1967), pp. 1591–1596.

Primary Examiner—John M. Ford
Attorney, Agent, or Firm—Sprung Horn Kramer & Woods

[57] ABSTRACT

Fungicidal pyridinylpyrimidines of the formula

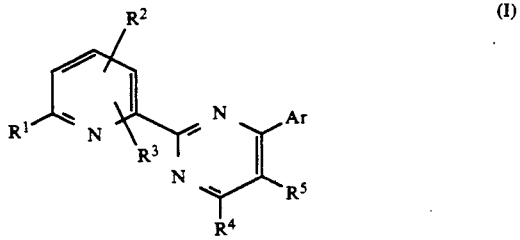

(I)

in which
R$^1$ represents hydrogen, halogen, alkoxy, alkylthio, halogenoalkyl, amino or dialkylamino, where, in the case of dialkylamino, the two radicals may, together with the nitrogen to which they are bonded, form a 5- to 7-membered, saturated or unsaturated ring which optionally contains a further hetero atom and which is optionally substituted by 1 or 2 alkyl groups; or
R$^1$ represents in each case optionally substituted aryloxy, arylthio, aralkyloxy or aralkylthio,
R$^2$ and R$^3$ are independent of one another and are identical or different and in each case represent hydrogen, halogen, alkyl, halogenoalkyl, alkoxy, alkylthio or alkoxycarbonyl, or
R$^2$ and R$^3$ together represent anaylene chain having 3 to 6 carbon atoms which are linked via the ring positions 3 and 4 or 4 and 5,
R$^4$ represents hydrogen, halogen, alkyl, halogenoalkyl, hydroxyl, alkoxy, mercapto, alkylthio, amino or (di)alkylamino, where, in the case of dialkylamino, the two radicals may, together with the nitrogen atom to which they are bonded, form a 5- to 7-membered, 4-phenyl-2-(2-pyridyl)-pyrimidine and 4-chloro-6-phenyl-2-(2-pyridyl)-pyrimidine (disclosed in J. Org. Chem. 32 (5), 1591–6 (1967)).

Furthermore, it has been found that the new pyridinylpyrimidine derivatives of the formula (I)

(Abstract continued on next page.)

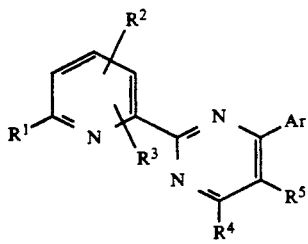 (I)

in which
R¹ represents hydrogen, halogen, alkoxy, alkylthio, halogenoalkyl, amino or dialkylamino, where, in the case of dialkylamino, the two radicals may, together with the nitrogen atom to which they are bonded, form a 5- to 7-membered, saturated or unsaturated ring which optionally contains a further hetero atom and which is optionally substituted by 1 or 2 alkyl groups;

in which furthermore
R¹ represents in each case optionally substituted aryloxy, arylthio, aralkyloxy or aralkylthio,
R² and R³ are independent of one another and are identical or different and in each case represent hydrogen, halogen, alkyl, halogenoalkyl, alkoxy, alkylthio or alkoxycarbonyl, or
R² and R³ together represent an alkylene chain having 3 to 6 carbon atoms which are linked via the ring positions or
R² and R³ together represent an alkylene chain having 3 to 6 carbon atoms which are linked via the ring positions 3 and 4 or 4 and 5,
R⁵ represents hydrogen or alkyl and
Ar represents unsubstituted or substituted aryl.

18 Claims, No Drawings

FUNGICIDAL PYRIDINYLPYRIMIDINES

CROSS REFERENCE TO RELATED APPLICATION

This application is a Continuation-In-Part of applicant's co-pending parent application Ser. No. 608,100 filed Oct. 31, 1990, now abandoned.

BACKGROUND OF THE INVENTION

The invention relates to new pyridinylpyrimidine derivatives, to a plurality of processes for their preparation, and to their use as pesticides, in particular as fungicides.

It is known that certain pyridinylpyrimidine derivatives, such as, for example, 2-(6-methyl-2-pyridinyl)-4-o-tolylpyrimidine, 2-(6-methyl-2-pyridinyl)-4-hydroxy-6-phenylpyrimidine (cf. EP 0,270,362)and 2-(6-phenyl-2-pyridinyl)-4-chloro-6-methylpyrimidine (cf. EP 0,259,139), have fungicidal properties.

However, the fungicidal activity of these previously known compounds is not entirely satisfactory in all fields of application.

4-Phenyl-2-(2-pyridyl)-pyrimidine and 4-chloro-6-phenyl-2-(2-pyridyl)-pyrimidine (cf. J. Org. Chem. 32 (5), 1591-6 (1967)) are furthermore known. However, nothing is reported about the physiological activity of these compounds.

New pyridinylpyrimidine derivatives of the general formula (I)

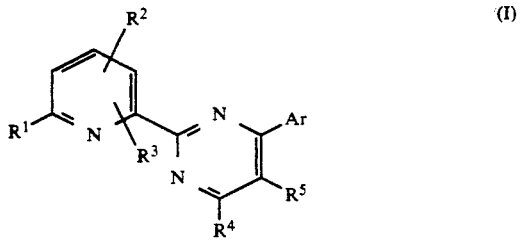

in which
R$^1$ represents hydrogen, halogen, alkoxy, alkylthio, halogenoalkyl, amino or dialkylamino, where, in the case of dialkylamino, the two radicals may, together with the nitrogen to which they are bonded, form a 5- to 7-membered, saturated or unsaturated ring which optionally contains a further hetero atom and which is optionally substituted by 1 or 2 alkyl groups;
in which furthermore
R$^1$ represents in each case optionally substituted aryloxy, arylthio, aralkyloxy or aralkylthio,
R$^2$ and R$^3$ are independent of one another and are identical or different and in each case represent hydrogen, halogen, alkyl, halogenoalkyl, alkoxy, alkylthio or alkoxycarbonyl,
or
R$^2$ and R$^3$ together represent an alkylene chain having 3 to 6 carbon atoms which are linked via the ring positions 3 and 4 or 4 and 5,
R$^4$ represents hydrogen, halogen, alkyl, halogenoalkyl, hydroxyl, alkoxy, mercapto, alkylthio, amino or (di)-alkylamino, where, in the case of dialkylamino, the two radicals may, together with the nitrogen atom to which they are bonded, form a 5- to 7-membered, saturated or unsaturated ring which optionally contains a further hetero atom and which is optionally substituted by 1 or 2 alkyl groups; or
R$^4$ represents alkenyloxy or alkynyloxy,
R$^5$ represents hydrogen or alkyl and
Ar represents unsubstituted or substituted aryl, have been found, with the exception of the compounds 4-phenyl-2-(2-pyridyl)-pyrimidine and 4-chloro-6-phenyl-2-(2-pyridyl)-pyrimidine (disclosed in J. Org. Chem. 32 (5), 1591-6 (1967)).

Furthermore, it has been found that the new pyridinylpyrimidine derivatives of the formula (I)

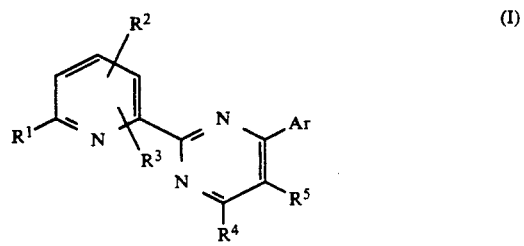

in which
R$^1$ represents hydrogen, halogen, alkoxy, alkylthio, halogenoalkyl, amino or dialkylamino, where, in the case of dialkylamino, the two radicals may, together with the nitrogen atom to which they are bonded, form a 5- to 7-membered, saturated or unsaturated ring which optionally contains a further hetero atom and which is optionally substituted by 1 or 2 alkyl groups;
in which furthermore
R$^1$ represents in each case optionally substituted aryloxy, arylthio, aralkyloxy or aralkylthio,
R$^2$ and R$^3$ are independent of one another and are identical or different and in each case represent hydrogen, halogen, alkyl, halogenoalkyl, alkoxy, alkylthio or alkoxycarbonyl,
or
R$^2$ and R$^3$ together represent an alkylene chain having 3 to 6 carbon atoms which are linked via the ring positions 3 and 4 or 4 and 5,
R$^4$ represents hydrogen, halogen, alkyl, halogenoalkyl, hydroxyl, alkoxy, mercapto, alkylthio, amino or (di)alkylamino, where, in the case of dialkylamino, the two radicals may, together with the nitrogen atom to which they are bonded, form a 5- to 7-membered, saturated or unsaturated ring which optionally contains a further hetero atom and which is optionally substituted by 1 or 2 alkyl groups; or
R$^4$ represents alkenyloxy or alkynyloxy,
R$^5$ represents hydrogen or alkyl and
Ar represents unsubstituted or substituted aryl, are obtained by one of the processes described below.

A) Pyridinylpyrimidine derivatives of the formula (Ia)

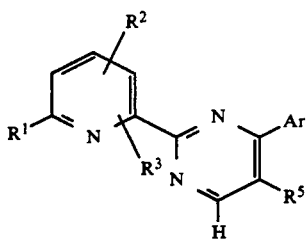

(Ia)

in which H
R$^1$, R$^2$, R$^3$, R$^5$ and Ar have the abovementioned meanings, are obtained when halogen-substituted pyridinylpyrimidine derivatives of the formula (II)

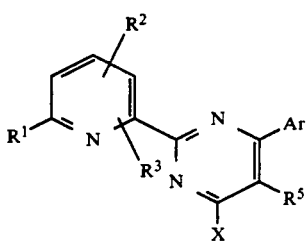

(II)

in which
R$^1$, R$^2$, R$^3$, R$^5$ and Ar have the abovementioned meaning and
X represents halogen,
are dehalogenated in the presence of a catalyst and under hydrogen pressure, if appropriate in the presence of a solvent and if appropriate in the presence of a base, B) pyridinylpyrimidine derivatives of the formula (Ib)

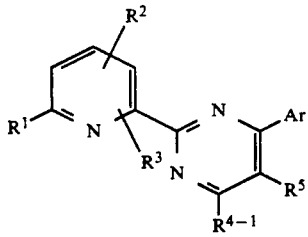

(Ib)

in which
R$^1$, R$^2$, R$^3$, R$^5$ and Ar have the abovementioned meanings and
R$^{4-1}$ represents mercapto, alkoxy, alkylthio, amino or (di)alkylamino, where, in the case of dialkylamino, the two radicals may, together with the nitrogen atom to which they are bonded, form a 5- to 7-membered, saturated or unsaturated ring which optionally contains a further hetero atom and which is optionally substituted by 1 or 2 alkyl groups, or represents alkenyloxy or alkynyloxy,
are obtained when halogen-substituted pyridinylpyrimidine derivatives of the formula (II)

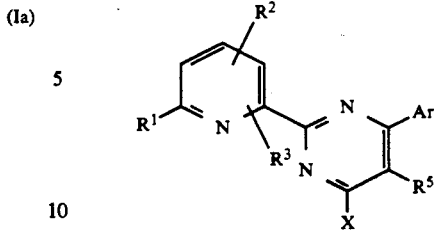

(II)

in which
R$^1$, R$^2$, R$^3$, R$^5$ and Ar have the abovementioned meanings and
X represents halogen,
are reacted with compounds of the formula (III)

R$^{4-1}$—M  (III)

in which
R$^{4-1}$ has the abovementioned meaning and
M represents hydrogen, or represents an alkali metal cation,
if appropriate in the presence of a diluent and if appropriate in the presence of a base, or C) pyridinylpyrimidine derivatives of the formula (Ic)

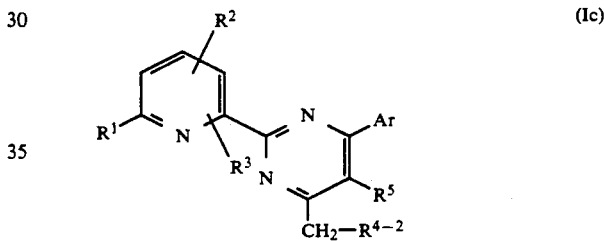

(Ic)

in which
R$^1$, R$^2$, R$^3$, R$^5$ and Ar have the abovementioned meanings and
R$^{4-2}$ represents hydrogen or alkyl,
are obtained when halogen-substituted pyridinylpyrimidine derivatives or the formula (II);

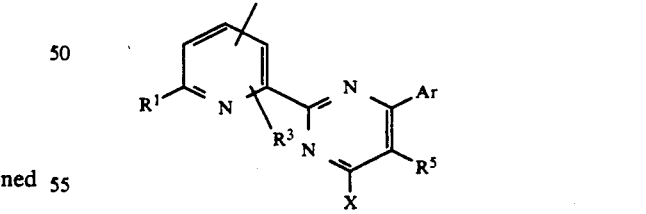

(II)

in which
R$^1$, R$^2$, R$^3$, R$^5$ and Ar have the abovementioned meanings and
X represents halogen, are reacted with diester derivatives of the formula (IV)

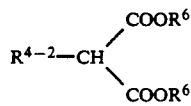

(IV)

in which

R$^{4\text{-}2}$ has the abovementioned meaning and

R$^6$ represents methyl or ethyl, if appropriate in the presence of a diluent and if appropriate in the presence of a base, and the resulting substituted pyridinylpyrimidines are hydrolyzed, if appropriate in the presence of a diluent and in the presence of a base, and the products are subsequently decarboxylated in the presence of an acid; or D) the pyridinylpyrimidine derivatives of the formula (Id)

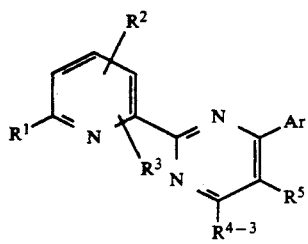

in which

R$^1$, R$^2$, R$^3$, R$^5$ and Ar have the abovementioned meanings and

R$^{4\text{-}3}$ represents hydrogen, alkyl or halogenoalkyl, are obtained when picolineamidine derivatives of the formula (V)

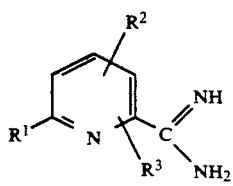

in which

R$^1$, R$^2$ and R$^3$ have the abovementioned meanings, or their acid addition salts α) are cyclized with aryl ketones of the formula (VI)

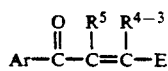

in which

R$^5$ and Ar have the abovementioned meanings,

R$^{4\text{-}3}$ represents hydrogen, alkyl or halogenoalkyl and

E represents a leaving group, if appropriate in the presence of a diluent and if appropriate in the presence of a base, or β) are reacted with acetals of the formula (VII)

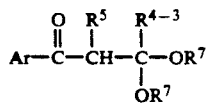

in which

R$^5$ and Ar have the abovementioned meanings,

R$^{4\text{-}3}$ represents hydrogen, alkyl or halogenoalkyl and

R$^7$ represents alkyl having 1 to 4 carbon atoms, if appropriate in the presence of a diluent and if appropriate in the presence of a base, γ) are reacted with 1,3-dioxo derivatives of the formula (VIII)

in which

R$^5$ and Ar have the abovementioned meanings and

R$^{4\text{-}3}$ represents hydrogen, alkyl or halogenoalkyl, if appropriate in the presence of a diluent and in the presence of a base, or δ) are reacted with diacetals of the formula (IX)

in which

Ar and R$^5$ have the abovementioned meanings,

R$^{4\text{-}3}$ represents hydrogen, alkyl or halogenoalkyl and

R$^8$ represents alkyl having 1 to 4 carbon atoms, if appropriate in the presence of a diluent.

Finally, it has been found that the new pyridinylpyrimidine derivatives of the formula (I) have a good action against plant diseases.

Surprisingly, the pyridinylpyrimidine derivatives of the general formula (I) according to the invention have a considerably more powerful fungicidal activity than the pyridinylpyrimidine derivatives known from the prior art, such as, for example, 2-(6-methyl-2-pyridinyl)-4-hydroxy-6-phenylpyrimidine, 2-(6-methyl-2-pyridinyl)-4-o-tolylpyrimidine or 2-(6-phenyl-2-pyridinyl)-4-chloro-6-methylpyrimidine, which are similar compounds chemically and from the point of view of their action.

Preferred substituents or areas of the radicals mentioned in the formulae given above and below are illustrated in the following:

The term alkyl in the definitions of R$^1$, R$^2$, R$^3$, R$^4$ and R$^5$ in the general formulae represents straight-chain or branched alkyl having preferably 1 to 6, particularly preferably 1 to 4 and in particular 1 or 2, carbon atoms. The following may be mentioned by way of example: methyl, ethyl, n-propyl, i-propyl, n-butyl, sec-butyl, i-butyl, t-butyl, n-pentyl and t-pentyl. The term alkenyloxy in the definition of R$^4$ in the general formulae represents straight-chain or branched alkenyloxy having preferably 2 to 6, particularly preferably 2 to 4 and very particularly preferably 2 or 3, carbon atoms. The following may be mentioned by way of example: vinyloxy, allyloxy, 2-propenyloxy, 1-butenyloxy, 2-butenyloxy, 3-butenyloxy and 1-methallyloxy.

The term alkynyloxy in the definition of R$^4$ in the general formulae represents straight-chain or branched alkynyloxy having preferably 2 to 6, particularly preferably 2 to 4 and very particularly preferably 2 or 3, carbon atoms. The following may be mentioned by way of example: 2-propynyloxy, 1-butynyloxy, 2-butynyloxy and 3-butynyloxy.

The term (di)alkylamino in the definitions of R$^1$ and R$^4$ in the general formulae represents an amino group having 1 or 2 alkyl groups, each of which can be straight-chain or branched and identical or different and each of which preferably contains 1 to 6, in particular 1 to 4 carbon atoms, of which groups methyl, ethyl, n- and i-propyl may be mentioned. The following may be mentioned by way of example: methylamino, dimethylamino, ethylamino, diethylamino, n-propylamino, di-n-propylamino, i-propylamino and di-i-propylamino.

If, in the case of dialkylamino, the two radicals together with the nitrogen atom to which they are bonded form a ring, the latter contains 5 to 7, preferably 5 or 6, ring members. The ring can contain 1 to 3 double bonds, but it is preferably saturated. The ring can contain a further hetero atom, preferably oxygen, sulphur or nitrogen, and it can be substituted by 1 or 2 alkyl groups, preferably by one alkyl group. The following may be mentioned by way of example: pyrrolidino, piperidino, morpholino, N-methylpiperazino, thiomorpholino and 2,6-dimethylmorpholino.

The term unsubstituted or substituted aryl in the definition of Ar in the general formulae is understood as meaning aryl having preferably 6 to 10 carbon atoms in the aryl moiety. The following may be mentioned by way of example and as preferred: unsubstituted or substituted phenyl or naphthyl, in particular phenyl.

The term halogenoalkyl in the definitions of $R^1$, $R^2$, $R^3$ and $R^4$ in the general formulae preferably represents straight-chain or branched alkyl having in each case 1 to 6 carbon atoms, particularly preferably having 1 to 4 carbon atoms, and in each case 1 to 13, preferably 1 to 6, identical or different halogen atoms, as defined under halogen; the following may be mentioned by way of example and as preferred: fluoromethyl, chloromethyl, bromomethyl, fluoroethyl, chloroethyl, bromoethyl, fluoro-n-propyl, chloro-n-propyl, difluoromethyl, trifluoromethyl, dichloromethyl, trichloromethyl, difluoroethyl, trifluoroethyl, trichloroethyl, chlorodifluoromethyl, trifluorochloroethyl, chlorobutyl and fluorobutyl.

The term alkoxy in the definitions of $R^1$, $R^2$, $R^3$ and $R^4$ in the general formulae is understood as meaning straight-chain or branched alkoxy having preferably 1 to 6, in particular 1 to 4, carbon atoms. The following may be mentioned by way of example: methoxy, ethoxy, propoxy, butoxy, as well as their isomers, i-propoxy, i-, s- and t-butoxy.

The term alkylthio in the definitions of $R^1$, $R^2$, $R^3$ and $R^4$ in the general formulae is understood as meaning straight-chain or branched alkylthio having preferably 1 to 6 carbon atoms, in particular 1 to 4 carbon atoms. The following may be mentioned by way of example: methylthio-, ethylthio-, propylthio-, butylthio-, pentylthio as well as their isomers, such as, for example, i-propylthio and i-, s- and t-butylthio. The following are particularly preferred: methylthio, ethylthio, tetrafluoroethylthio, trichloroethylthio, chlorodifluoromethylthio and trifluorochloroethylthio.

The term alkoxycarbonyl in the definitions of $R^2$ and $R^3$ in the general formulae is understood as meaning straight-chain or branched alkoxycarbonyl having 1 to 6, preferably 1 to 4, carbon atoms in the alkoxy radical. The following may be mentioned by way of example: methoxycarbonyl, ethoxycarbonyl, n-propoxycarbonyl, i-propoxycarbonyl, n-, i-, s- and t-butoxycarbonyl.

Unsubstituted or substituted aryloxy and arylthio in the definition of $R^1$ in the general formulae generally represents aryl having preferably 6 to 10 carbon atoms in the aryl moiety. The following may be mentioned by way of example: unsubstituted or substituted phenoxy or phenylthio.

In general, unsubstituted or substituted aralkyloxy or aralkylthio in the definition of $R^1$ preferably contain 1 to 6 carbon atoms in the straight-chain or branched alkyl moiety and preferably phenyl as the aryl moiety. Aralkyloxy or aralkylthio groups which may be mentioned by way of example are benzyloxy and benzylthio.

Halogen in the definitions of $R^1$, $R^2$, $R^3$ and $R^4$ in the general formulae represents fluorine, chlorine, bromine and iodine, preferably fluorine, chlorine and bromine.

The substituents of the aryl radicals as such or in combinations such as aryloxy, arylthio, aralkyloxy and aralkylthio have the meanings indicated below.

Halogen as a substituent generally represents fluorine, chlorine, bromine and iodine, preferably fluorine, chlorine and bromine, particularly preferably fluorine and chlorine.

Alkyl as a substituent or in combinations such as phenylalkylthio or phenylalkyloxy generally represents straight-chain or branched alkyl, preferably having 1 to 6, particularly preferably having 1 to 4, carbon atoms, methyl and ethyl being very particularly preferred. The enumeration by way of example corresponds to that given hereinabove.

Alkoxy as a substituent generally represents straight-chain or branched alkoxy having 1 to 6, particularly preferably to 4, carbon atoms per alkyl radical; the following may be mentioned by way of example and as being preferred: methoxy, ethoxy, n- and i- propoxy, n-, i-, s- and t-butoxy, n-hexoxy and i-hexoxy.

Alkylthio as a substituent in the radicals generally represents straight-chain or, branched alkylthio having preferably 1 to 6 carbon atoms, for example it is understood as meaning the following groups: methylthio, ethylthio, propylthio, butylthio, pentylthio as well as their isomers, such as, for example, i-propylthio, i-, s- and t-butylthio, 1-methyl-butylthio, 2-methyl-butylthio- and 2-methyl-butylthio. Preferred alkylthio radicals contain 1 to 4 carbon atoms. The following are particularly preferred: methylthio, ethylthio, n-, i-, s- propylthio and n-, i-, s- and t-butylthio.

Alkoxycarbonyl as a substituent in the radicals generally represents straight-chain or branched alkoxycarbonyl having 1 to 6, preferably 1 to 4, carbon atoms in the alkoxy radical; the following may be mentioned by way of example: methoxycarbonyl, ethoxycarbonyl, n-propoxycarbonyl, i-propoxycarbonyl, n-, i-, s- and t-butoxycarbonyl.

Cycloalkyl as a substituent in the radicals generally represents cycloalkyl having preferably 3 to 7, in particular 3, 5 or 6, carbon atoms. The following may be mentioned by way of example: unsubstituted or substituted cyclopropyl, cyclobutyl, cyclopentyl, cyclohexyl and cycloheptyl.

Alkenyl and alkynyl as substituents in the radicals generally represent straight-chain or branched alkenyl or alkynyl having preferably 2 to 6, particularly preferably 2 to 4 and very particularly preferably 2 or 3, carbon atoms. The following may be mentioned by way of example: vinyl, allyl, prop-2-enyl, 1-butenyl, 2-butenyl, 3-butenyl, ethynyl, 1-propynyl, 2-propynyl, 1-butynyl, 2-butynyl and 3-butynyl.

Akenyloxy and alkynyloxy as substituents in the radicals generally represent straight-chain or branched alkenyloxy or alkynyloxy having preferably 2 to 6, particularly preferably 2 to 4 and very particularly preferably 3, carbon atoms. The following may be mentioned by way of example: alkyloxy, 2-propenyloxy, 2-butenyloxy, 2-propynyloxy and 2-butynyloxy.

Halogenoalkyl and halogenoalkoxy as substituents in the radicals generally represent straight-chain or branched halogenoalkyl or halogenoalkoxy having in each case 1 to 6 carbon atoms, particularly preferably having 1 to 4 carbon atoms, and in each case 1 to 13, preferably 1 to 9, identical or different halogen atoms as defined under halogen; the following may be mentioned by way of example: fluoromethyl, chloromethyl, bromomethyl, fluoroethyl, chloroethyl, bromoethyl, fluoro-n-propyl, chloro-n-propyl, difluoromethyl, trifluoromethyl, dichloromethyl, trichloromethyl, difluoroethyl, trifluoroethyl, trichloroethyl, chlorodifluoro-methyl, trifluorochloroethyl, chlorobutyl, fluorobutyl, fluoromethoxy, chloromethoxy, bromomethoxy, fluoroethoxy, chloroethoxy, bromoethoxy, fluoropropoxy, chloropropoxy, bromopropoxy, fluorobutoxy, chlorobutoxy, fluoro-i-propoxy, chloro-i-propoxy, difluoromethoxy, trifluoromethoxy, dichloromethoxy, trichloromethoxy, difluoroethoxy, trifluoroethoxy, tetrafluoroethoxy, trichloroethoxy, chlorodifluoromethoxy and trifluorochloroethoxy.

Halogenoalkylthio as a substituent in the radicals generally represents straight-chain or branched halogenoalkylthio in each case having 1 to 6 carbon atoms, particularly preferably 1 to 4 carbon atoms, and in each case 1 to 13, preferably 1 to 9, identical or different halogen atoms as defined under halogen; the following may be mentioned by way of example: fluoromethylthio, chloromethylthio, bromomethylthio, fluoroethylthio, chloroethylthio, bromoethylthio, fluoropropylthio, chloropropylthio, bromopropylthio, fluorobutylthio, chlorobutylthio, bromobutylthio, fluoro-i-propylthio, chloro-i-propylthio, difluoromethylthio, trifluoromethylthio, dichloromethylthio, trichloromethylthio, difluoroethylthio, trifluoroethylthio, tetrafluoroethylthio, trichloroethylthio, chlorodifluoromethylthio and trifluorochloroethylthio.

(Di)alkylamino as a substituent in the radicals generally represents an amino group having 1 or 2 alkyl groups, each of which can be straight-chain or branched and identical or different, and each of which preferably contains 1 to 6, in particular 1 to 4, carbon atoms, of which groups methyl, ethyl, and n- and i-propyl may be mentioned. Examples which may be given are methylamino, ethylamino, n-propylamino, i-propylamino, dimethylamino, diethylamino, di-n-propylamino and di-i-propylamino.

If, in the case of dialkylamino, the two radicals together with the nitrogen atom to which they are bonded form a ring, the latter contains 5 to 7, preferably 5 or 6, ring members. The ring can contain 1 to 3 double bonds, but it is preferably saturated. The ring can contain a further hetero atom, preferably oxygen, sulphur or nitrogen, and it can be substituted by 1 or 2 alkyl groups, preferably by one alkyl group. The following may be mentioned by way of example: pyrrolidino, piperidino, morpholino, N-methylpiperazino, thiomorpholino and 2,6-dimethylmorpholino.

(Di)alkylaminocarbonyl as a substituent in the radicals generally represents an aminocarbonyl group having 1 or 2 alkyl groups, each of which can be straight-chain or branched and identical or different, and each of which preferably contains 1 to 6, in particular 1 to 4, carbon atoms, of which groups methyl, ethyl, and n- and i-propyl may be mentioned. The following may be mentioned by way of example: methylaminocarbonyl, ethylaminocarbonyl, dimethylaminocarbonyl and diethylaminocarbonyl.

If, in the case of dialkylamino, the two radicals together with the nitrogen atom to which they are bonded form a ring, the latter contains 5 to 7, preferably 5 or 6, ring members. The ring can contain 1 to 3 double bonds, but it is preferably saturated. The ring can contain a further hetero atom, preferably oxygen, sulphur or nitrogen, and it can be substituted by 1 or 2 alkyl groups, preferably by one alkyl group. The following may be mentioned by way of example: pyrrolidino, piperidino, morpholino, n-methylpiperazino, thiomorpholino and 2,6-dimethylmorpholino.

Alkylcarbonylamino as a substituent in the radicals generally represents straight-chain or branched alkylcarbonylamino having 1 to 6, preferably 1 to 4, carbon atoms in the alkyl radical; the following may be mentioned by way of example: methylcarbonylamino, ethylcarbonylamino, n-propylcarbonylamino, i-propylcarbonylamino.

Alkylhydrazo as a substituent in the radicals generally represents straight-chain or branched alkylhydrazo having 1 to 6, preferably 1 to 4, carbon atoms in the alkyl moiety. The following may be mentioned by way of example: 2-methylhydrazo, 2-ethylhydrazo, 2-propylhydrazo and 2,2-dimethylhydrazo.

Formula (I) provides a general definition of the pyridinylpyrimidine derivatives according to the invention. Preferred compounds of the formula (I) are those in which $R^1$ represents hydrogen, halogen, in each case straight-chain or branched alkoxy or alkylthio each of which has 1 to 6 carbon atoms, or represents straight-chain or branched halogenoalkyl having 1 to 6 carbon atoms and 1 to 13 identical or different halogen atoms, amino, alkylamino or dialkylamino each of which has 1 to 6 carbon atoms in the respective straight-chain or branched alkyl moieties, where, in the case of dialkylamino, the two radicals may, together with the nitrogen atom to which they are bonded, form a 5- or 6-membered saturated or unsaturated ring which optionally contains an oxygen, sulphur or nitrogen atom and which is optionally substituted by 1 or 2 alkyl groups having 1 or 2 carbon atoms; or furthermore represents phenoxy or phenylthio, each of which is optionally monosubstituted or polysubstituted by identical or different substituents, phenyl substituents which may be mentioned being: halogen, cyano, nitro, alkyl, alkoxy or alkylthio each of which has 1 or 2 carbon atoms, and also halogenoalkyl, halogenoalkoxy or halogenoalkylthio each of which has 1 or 2 carbon atoms and each of which has 1 to 5 fluorine and/or chlorine atoms, or $R^1$ represents phenylalkoxy or phenylalkylthio each of which has 1 to 4 carbon atoms in the respective straight-chain or branched alkyl moiety and each of which is optionally monosubstituted or polysubstituted by identical or different substituents, suitable substituents of the phenyl moiety being the above-mentioned phenyl substituents, $R^2$ and $R^3$ are independent of one another and identical or different and in each case represent hydrogen, halogen, straight-chain or branched alkyl having 1 to 6 carbon atoms, or represent straight-chain or branched halogenoalkyl having 1 to 6 carbon atoms and 1 to 13 identical or different halogen atoms, or represent in each case straight-chain or branched alkoxy or alkylthio each of which has 1 to 6 carbon atoms, or represent straight-chain or branched alkoxycarbonyl having 1 to 6 carbon atoms in the alkoxy moiety, or $R^2$ and $R^3$ together represent an alkyl chain which has 3 to 5 carbon atoms and which is linked via the ring positions 3 and 4 or 4 and 5, $R^4$ represents hydrogen, halogen, straight-chain or branched alkyl having 1 to 6 carbon atoms, straight-chain or branched halogenoalkyl having 1 to 6 carbon atoms and 1 to 13 identical or different halogen atoms, hydroxyl, mercapto, in each case straight-chain or branched alkoxy or alkylthio each of which has 1 to 6 carbon atoms, amino, alkylamino or dialkylamino each of which has 1 to 6 carbon atoms in the respective straight-chain or branched alkyl moieties, where, in the case of dialkylamino, the two radicals may, together with the nitrogen atom to which they are bonded, form a 5- or 6-membered saturated or unsaturated ring which optionally contains an oxygen, sulphur or nitrogen atom and which is optionally substituted by 1 or 2 alkyl groups having 1 or 2 carbon atoms, or represents in each case straight-chain or branched alkenyloxy or alkynyloxy each of which has 2 to 6 carbon atoms, $R^5$ represents hydrogen or straight-chain or branched alkyl having 1 to 6 carbon atoms, and Ar represents phenyl which is optionally mono-substituted or polysubstituted by identical or different substituents, substituents which may be mentioned being:

halogen, cyano, nitro, hydroxyl, amino, mercapto, straight-chain or branched alkyl having 1 to 6 carbon atoms, straight-chain or branched halogenoalkyl having 1 to 6 carbon atoms and 1 to 13 identical or different halogen atoms, in each case straight-chain or branched alkoxy or alkylthio each of which has 1 to 6 carbon atoms, in each case straight-chain or branched halogenoalkylthio or halogenoalkoxy each of which has 1 to 6 carbon atoms and each of which has 1 to 13 identical or different halogen atoms, in each case straight-chain or branched alkenyl or alkynyl having 2 to 6 carbon atoms, in each case straight-chain or branched alkenyloxy or alkinyloxy having 2 to 6 carbon atoms, cycloalkyl having 3 to 8 carbon atoms, phenyl, phenoxy, phenylthio, phenylalkylthio or phenylalkyloxy each of which has 1 to 4 carbon atoms in the straight-chain or branched alkyl moiety, phenyl substituents which may furthermore be mentioned being:

(di)alkylamino having 1 to 6 carbon atoms in the respective straight-chain or branched alkyl moieties, where, in the case of dialkylamino, the two radicals may, together with the nitrogen atom to which they are bonded, form a 5- or 6-membered saturated or unsaturated ring which optionally contains an oxygen, sulphur or nitrogen atom and which is optionally substituted by 1 or 2 alkyl groups having 1 or 2 carbon atoms, or furthermore phenylamino, hydrazino which is optionally monosubstituted or disubstituted by straight-chain or branched alkyl having 1 to 6 carbon atoms or by phenyl, or alkyl- or phenylcarbonylamino having 1 to 6 carbon atoms in the straight-chain or branched alkyl moiety, aminocarbonyl, (di)alkylaminocarbonyl having 1 to 6 carbon atoms in the respective straight-chain or branched alkyl moieties, where, in the case of dialkylaminocarbonyl, the two radicals may, together with the nitrogen atom to which they are bonded, form a 5- or 6-membered saturated or unsaturated ring which optionally contains an oxygen, sulphur or nitrogen atom and which is optionally substituted by 1 or 2 alkyl groups having 1 or 2 carbon atoms, or straight-chain or branched alkoxycarbonyl having 1 to 6 carbon atoms, or two adjacent phenyl substituents together represent alkanediyl having 1 to 6 carbon atoms which optionally contains one or more hetero atoms from the series comprising oxygen, sulphur and nitrogen.

Particularly preferred compounds of the formula (I) are those in which $R^1$ represents hydrogen, fluorine, chlorine, bromine, in each case straight-chain or branched alkoxy or alkylthio each of which has 1 to 4 carbon atoms, or represents straight-chain or branched halogenoalkyl having 1 to 4 carbon atoms and 1 to 9 fluorine and/or chlorine atoms, or amino, alkylamino or dialkylamino each of which has 1 to 4 carbon atoms in the respective straight-chain or branched alkyl moieties, where, in the case of dialkylamino, the two radicals may, together with the nitrogen atom to which they are bonded, form a 5- or 6-membered saturated ring which optionally contains an oxygen, sulphur or nitrogen atom and which is optionally substituted by 1 or 2 methyl groups, furthermore represents phenoxy or phenylthio each of which is optionally monosubstituted or disubstituted by identical or different substituents, suitable phenyl substituents which may be mentioned being: fluorine, chlorine, bromine, cyano, nitro, methyl, trifluoromethyl, methoxy, trifluoromethoxy, methylthio or trifluoromethylthio, or $R^1$ represents phenylalkoxy phenylalkylthio each of which has 1 or 2 carbon atoms in the alkyl moiety and each of which is optionally monosubstituted or disubstituted by identical or different substituents, suitable substituents of the phenyl moiety being the above-mentioned phenyl substituents.

$R^2$ represents hydrogen, fluorine, chlorine or bromine, or represents straight-chain or branched alkyl, having 1 to 4 carbon atoms, straight-chain or branched halogenoalkyl having 1 to 4 carbon atoms and 1 to 9 fluorine and/or chlorine atoms, or represents in each case straight-chain or branched alkoxy or alkylthio having 1 to 4 carbon atoms, or represents straight-chain or branched alkoxycarbonyl having 1 to 4 carbon atoms in the alkoxy moiety, $R^3$ represents hydrogen, fluorine, chlorine, bromine or straight-chain or branched alkyl having 1 to 4 carbon atoms or $R^2$ and $R^3$ together represent an alkyl chain which has 3 or 4 carbon atoms and which is linked via the ring positions 3 and 4 or 4 and 5, $R^4$ represents hydrogen, fluorine, chlorine, bromine, straight-chain or branched alkyl having 1 to 4 carbon atoms, straight-chain or branched halogenoalkyl having 1 to 4 carbon atoms and 1 to 9 fluorine and/or chlorine atoms, hydroxyl, mercapto, in each case straight-chain or branched alkoxy or alkylthio having 1 to 4 carbon atoms, amino, alkylamino or dialkylamino each of which has 1 to 4 carbon atoms in the respective straight-chain or branched alkyl moieties, where, in the case of dialkylamino, the two radicals may, together with the nitrogen atom to which they are bonded, form a 5- or 6-membered saturated ring which optionally contains an oxygen, sulphur or nitrogen atom and which is optionally substituted by 1 or 2 methyl groups, or represents in each case straight-chain or branched alkenyloxy or alkynyloxy each of which has 3 or 4 carbon atoms, $R^5$ represents hydrogen or straight-chain or branched alkyl having 1 to 4 carbon atoms and Ar represents phenyl which is optionally monosubstituted to trisubstituted by identical or different substituents, substituents which may be mentioned being: fluorine, chlorine, bromine, iodine, cyano, nitro, hydroxyl, mercapto, amino, straight-chain or branched alkyl having 1 to 4 carbon atoms, straight-chain or branched halogenoalkyl having 1 to 4 carbon atoms and 1 to 9 fluorine and/or chlorine atoms, in each case straight-chain or branched alkoxy or alkylthio each of which has 1 to 4 carbon atoms, in each case straight-chain or branched halogenoalkoxy or halogenoalkylthio each of which has 1 to 4 carbon atoms and each of which has 1 to 9 fluorine and/or chlorine atoms, in each case straight-chain or branched alkenyl or alkynyl each of which has 2 to 4 carbon atoms, in each case straight-chain or branched alkenyloxy or alkinyloxy each of which has 3 to 4 carbon atoms, cycloalkyl having 3 to 6 carbon atoms, phenyl, phenoxy, phenylthio, phenylalkoxy or phenylalkylthio each of which has or 2 carbon atoms in the alkyl moiety; phenyl substituents which may furthermore be mentioned being:

(di)alkylamino having 1 to 4 carbon atoms in the respective straight-chain or branched alkyl moieties, where, in the case of dialkylamino, the two radicals may, together with the nitrogen atom to which they are bonded, form a 5- or 6-membered saturated ring which optionally contains an oxygen, sulphur or nitrogen atom and which is optionally substituted by 1 or 2 methyl groups; furthermore phenylamino, hydrazino which is optionally monosubstituted or disubstituted by straight-chain or branched alkyl having 1 to 4 carbon atoms or by phenyl, or alkyl- or phenylcarbonylamino having 1 to 4 carbon atoms in the straight-chain or branched alkyl moiety, aminocarbonyl, (di)alkylaminocarbonyl having 1 to 4 carbon atoms in the respective straight-chain or branched alkyl moieties, where, in the case of dialkylaminocarbonyl, the two radicals may, together with the nitrogen atom to which they are bonded, form a 5- or 6-membered saturated ring which optionally contains an oxygen, sulphur or nitrogen atom and which is optionally substituted by 1 or 2 methyl groups; and also straight-chain or branched alkoxycarbonyl having 1 to 4 carbon atoms, or two adjacent phenyl substituents together represent alkanediyl which has 1 to 4 carbon atoms and which optionally contains 1 or 2 hetero atoms from the series comprising oxygen, sulphur and nitrogen.

Very particularly preferred compounds of the formula (I) are those in which $R^1$ represents hydrogen, fluorine, chlorine, methoxy, ethoxy, n-propoxy or i-propoxy, methylthio, ethylthio, trifluoromethyl, trichloromethyl, difluoromethyl or chlorofluoromethyl, or represents methylamino, dimethylamino, ethylamino, diethylamino, pyrrolidino, piperidino, morpholino, thiomorpholino, n-methyl-piperazino, 2,6-dimethylmorpholino, or represents phenoxy, phenylthio, benzyloxy or benzylthio, $R^2$ represents hydrogen, fluorine, chlorine, bromine, methyl, ethyl, n-propyl or i-propyl, or represents trifluoromethyl, trichloromethyl, difluoromethyl, dichloromethyl, or represents methoxy or ethoxy, or represents methylthio, or represents methoxy- or ethoxycarbonyl, $R^3$ represents hydrogen, fluorine, chlorine, bromine, methyl, ethyl, n-propyl, i-propyl or t-butyl, $R^4$ represents hydrogen, fluorine, chlorine, bromine, methyl, trifluoromethyl, trichloromethyl, hydroxyl, mercapto, methoxy, ethoxy, n-propoxy, i-propoxy, methylthio, ethylthio, n-propylthio or i-propylthio, n-butylthio, i-butylthio, s-butylthio or t-butylthio, or represents amino, methylamino, ethylamino, dimethylamino, diethylamino, pyrrolidino, piperidino, morpholino, thiomorpholino, N-methylpiperazino or 2,6-dimethylmorpholino, or represents 2-propenyloxy or 2-propynyloxy, $R^5$ represents hydrogen, methyl, ethyl, n-propyl, i-propyl or n-butyl and Ar represents phenyl which is optionally monosubstituted to trisubstituted by identical or different substituents, substituents which may be mentioned being:

fluorine, chlorine, bromine, iodine, cyano, nitro, hydroxyl, amino, mercapto, methyl, ethyl, n-propyl or i-propyl, n-butyl, s-butyl, i-butyl or t-butyl, trifluoromethyl, trichloromethyl, difluoromethyl, methoxy, ethoxy, methylthio, ethylthio, trifluoromethoxy, difluoromethoxy, trifluoromethylthio, chlorodifluoromethylthio, vinyl, 2-propenyl, 2-propynyl, 2-propenyloxy, 2-propynyloxy, cyclopropyl, cyclopentyl, cyclohexyl, phenyl, phenoxy, phenylthio, phenylmethoxy or phenylmethylthio, further phenyl substituents which may be mentioned being:

methylamino, dimethylamino, ethylamino, diethylmino, pyrrolidino, piperidino, morpholino, thiomorpholino, N-methylpiperazino, 2,6-dimethylmorpholino, phenylamino, hydrazino, 2-methylhydrazo, 2,2-dimethylhydrazo, 2-phenylhydrazo, methylcarbonylamino, phenylcarbonylamino, aminocarbonyl, methylaminocarbonyl, dimethylaminocarbonyl, methoxycarbonyl or ethoxycarbonyl.

The following pyridinylpyrimidine derivatives of the general formula (I) may be mentioned individually in addition to the compounds mentioned in the preparation examples:

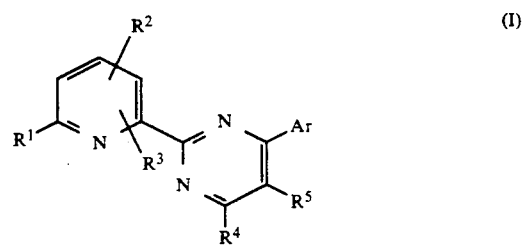

(I)

TABLE 1
| R¹ | R² | R³ | R⁴ | R⁵ | Ar |
|----|----|----|----|----|-----|
| Cl | H | H | CH₃O— | CH₃ | 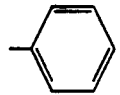 |
| Cl | H | H | C₂H₅O— | H | 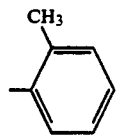 |
| Cl | H | H | —OCH₂—CH=CH₂ | H | 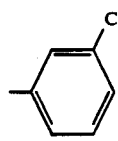 |
| Cl | 5-Cl | H | —OCH₂—C≡CH | H | 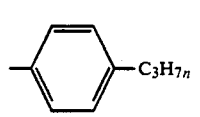 |
| Cl | 4-Cl | H | CH₃ | H | 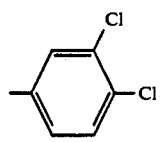 |
| Cl | 5-Cl | 3-Cl | H | CH₃ | 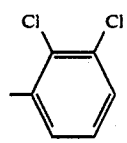 |
| Br | H | H | Br | —C₂H₅ | 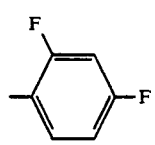 |
| Br | H | H | OH | CH₃ | 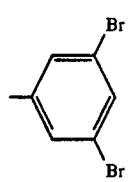 |
| Br | 5-CF₃ | H | H | H | 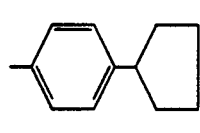 |
| Br | H | 3-CO₂CH₃ | CF₃ | H | 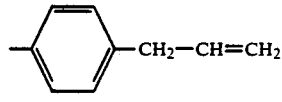 |
| F | 4-F | H | —SCH₃ | H | 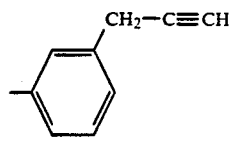 |

TABLE 1-continued
| R¹ | R² | R³ | R⁴ | R⁵ | Ar |
|---|---|---|---|---|---|
| F | 5-SCH₃ | H | —NHCH₃ | H | 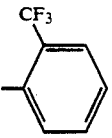 2-CF₃-phenyl |
| CH₃O— | H | H | —N(CH₃)₂ | H | 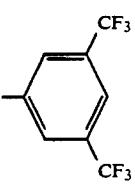 3,5-bis(CF₃)-phenyl |
| CH₃O— | H | 3-CH₃ | —NH₂ | H | 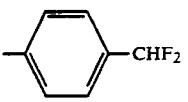 4-CHF₂-phenyl |
| CH₃O— | 5-C₂H₅ | H | —SH | H | 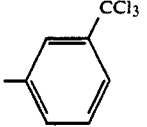 3-CCl₃-phenyl |
| CH₃O— | H | H | Cl | H | 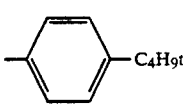 4-C₄H₉t-phenyl |
| C₂H₅O— | 4-C₂H₅O | H | Cl | H | 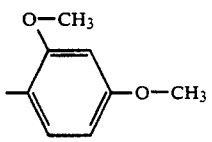 2,4-dimethoxyphenyl |
| C₂H₅O— | 4-Cl | H | F | H | 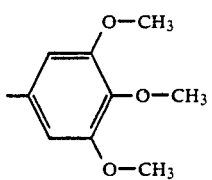 3,4,5-trimethoxyphenyl |
| n-C₃H₇O— | H | H | CH₃O— | H | 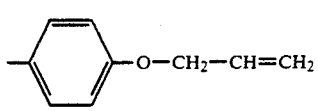 4-(O—CH₂—CH=CH₂)-phenyl |
| —SCH₃ | H | H | C₂H₅O— | H | 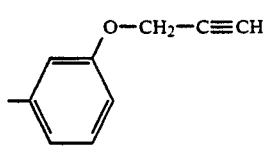 3-(O—CH₂—C≡CH)-phenyl |
| —SC₂H₅ | H | H | —CF₃ | H | 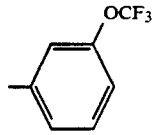 3-OCF₃-phenyl |
| —N(CH₃)₂ | H | H | —CCl₃ | H | 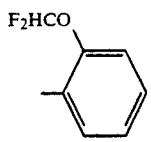 2-(F₂HCO)-phenyl |

TABLE 1-continued
| R¹ | R² | R³ | R⁴ | R⁵ | Ar |
|---|---|---|---|---|---|
| —CF₃ | H | H | n-C₃H₇O— | H | 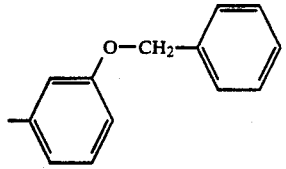 |
| —CF₃ | H | 3-OCH₃ | OH | H | 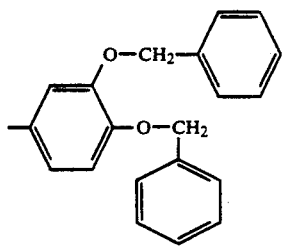 |
| —CHF₂ | H | H | CH₃ | CH₃ | 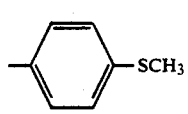 |
| —CCl₃ | H | H | H | C₂H₅ | 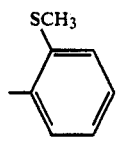 |
| —CHClF | H | 3-Cl | CH₃S— | H | 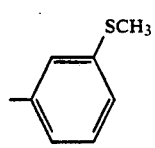 |
| H | 5-CH₃O— | 3-CH₃O— | SH | H | 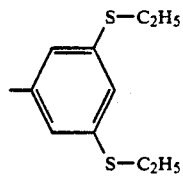 |
| 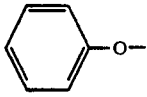 | H | H | —NH₂ | H | 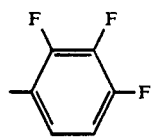 |
| 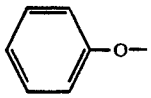 | H | H | CH₃O— | H | 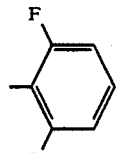 |
| 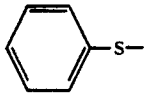 | H | H | CH₃O— | CH₃ | 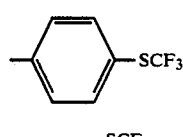 |
| 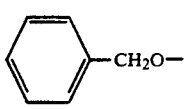 | H | H | C₂H₅O— | H | 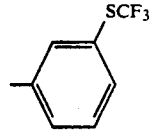 |

TABLE 1-continued

| R¹ | R² | R³ | R⁴ | R⁵ | Ar |
|---|---|---|---|---|---|
| C₆H₅—CH₂—S— | H | H | Cl | H | 3-(SCF₂Cl)-C₆H₄— |
| C₆H₅—CH₂—S— | H | 3-CF₃ | Cl | H | 4-(SCFCl₂)-C₆H₄— |
| H | 5-Cl | 4-Cl | H | H | 3-(S-CH₂-C₆H₅)-C₆H₄— |
| H | 5-Cl | 3-Cl | H | H | 3-(S-CH₂-C₆H₅)-5-(O-CH₂-C₆H₅)-C₆H₃— |
| H | H | 3-Br | H | H | 4-(O-C₆H₅)-C₆H₄— |
| H | H | 3-CH₃ | CH₃ | H | 4-(O-C₆H₅)-C₆H₄— |
| H | H | 3-CO₂—C₂H₅ | CH₃ | H | 4-biphenyl— |
| H | 5-CO₂—CH₃ | H | H | H | 3-biphenyl— |
| H | 5-CF₃ | H | OH | H | 4-(NH-C₆H₅)-C₆H₄— |
| Cl | 5-CF₃ | H | OH | H | 2-CH₃-3-CH₃-(NH-CH₃)-C₆H₃— |

TABLE 1-continued

| R¹ | R² | R³ | R⁴ | R⁵ | Ar |
|---|---|---|---|---|---|
| CH₃O— | 5-CF₃ | H | Cl | H | 4-N(CH₃)₂-C₆H₄— |
| Br | 5-CHF₂ | H | Cl | H | 3-N(C₂H₅)₂-C₆H₄— |
| Cl | 5-CCl₃ | H | Cl | H | 4-biphenyl |
| CH₃O— | 5-CCl₃ | H | Br | H | 3-biphenyl |
| F | 5-CHClF | H | H | CH₃ | 3,5-diphenylphenyl |
| CH₃S— | 5-CH₃ | H | H | CH₃ | 4-CN-C₆H₄— |
| H | 5-C₂H₅ | H | H | H | 3-NO₂-C₆H₄— |
| H | 5-Cl | H | H | H | 4-NO₂-C₆H₄— |
| Cl | 5-Cl | H | H | C₂H₅ | 2-CN-C₆H₄— |
| —N(CH₃)₂ | 5-Cl | H | H | H | 2-NO₂-C₆H₄— |

TABLE 1-continued

| $R^1$ | $R^2$ | $R^3$ | $R^4$ | $R^5$ | Ar |
|---|---|---|---|---|---|
| C₆H₅O— | 5-Cl | H | H | H | —C₆H₄-CO₂CH₃ (3-) |
| C₆H₅O— | 5-Br | H | H | H | —C₆H₄-CO₂—C₂H₅ (4-) |
| C₆H₅O— | 5-Br | H | CH₃ | H | —C₆H₄-CO—NH₂ (4-) |
| C₆H₅O— | 5-Br | H | CH₃O | H | —C₆H₄-CO—NH—CH₃ (4-) |
| H | 5-CH₃O— | H | CH₃O— | —C₃H₇-n | —C₆H₄-OH (4-) |
| —CF₃ | 5-C₂H₅O— | H | OH | H | —C₆H₂(OH)₃ (3,4,5-) |
| H | H | 4-Br | H | H | —C₆H₄-SH (4-) |
| H | H | 4-Br | CH₃ | H | —C₆H₄-SH (2-) |
| H | H | 4-Cl | CH₃O— | H | —C₆H₃(SH)₂ (2,6-) |
| H | H | 4-Cl | CH₃O— | H | —C₆H₄-NH₂ (2-) |
| H | H | 4-CF₃ | CH₃O— | H | —C₆H₄-NH—NH₂ (4-) |

TABLE 1-continued
| $R^1$ | $R^2$ | $R^3$ | $R^4$ | $R^5$ | Ar |
|---|---|---|---|---|---|
| H | H | 4-CHF$_2$ | n-C$_3$H$_7$S— | H | 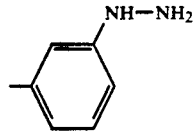 |
| H | H | 4-CHCl$_2$ | CH$_2$=CH—CH$_2$O— | H | 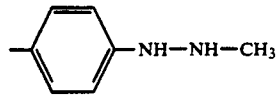 |
| H | 5-F | 4-CH$_3$ | n-C$_3$H$_7$O— | H | 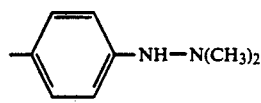 |
| H | 5-CH$_3$ | 4-CH$_3$ | i-C$_3$H$_7$O— | H | 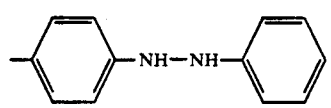 |
| H | H | 3-C$_2$H$_5$ | CH≡C—CH$_2$O— | H | 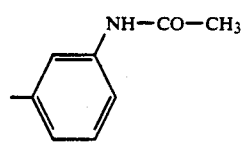 |
| H | H | 3-OCH$_3$ | CH$_3$S— | H | 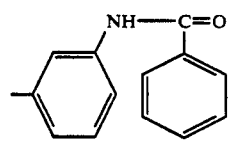 |
| H | H | 3-OCH$_3$ | CH$_3$CN— | H | 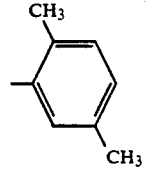 |
| H | H | 3-OC$_2$H$_5$ | (CH$_3$)$_2$N— | H | 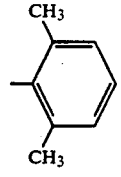 |
| H | H | 3-C$_3$H$_7$n | CH$_3$O— | H | 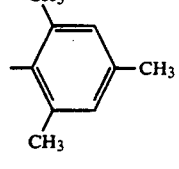 |
| H | H | 3-CF$_3$ | CH$_3$O— | CH$_3$ | 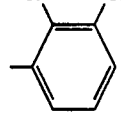 |

TABLE 1-continued
| $R^1$ | $R^2$ | $R^3$ | $R^4$ | $R^5$ | Ar |
|---|---|---|---|---|---|
| H | H | 3-$CF_3$ | $CH_3O-$ | $-C_2H_5$ | 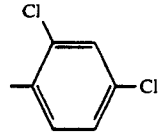 |
| H | H | 3-$CCl_3$ | $C_2H_5O-$ | H | 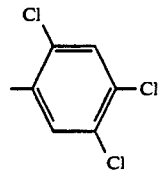 |
| H | H | 3-$CO_2-CH_3$ | SH | H | 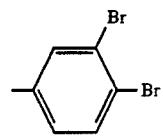 |
| H | H | 3-$CO_2-C_2H_5$ | $C_2H_5O-$ | H | 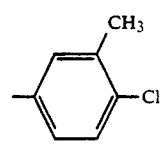 |
| H | H | 3-F | $CH_2=CH-CH_2O-$ | H | 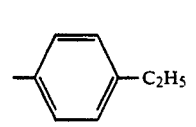 |
| H | 5-Cl | 3-Cl | H | $CH_3$ | 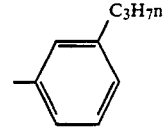 |
| H | 5-Br | 3-Br | H | H | 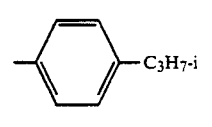 |
| H | 5-$CCl_3$ | 3-Cl | H | H | 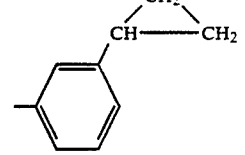 |
| H | 5-$CO_2-CH_3$ | 3-$C_2H_5O-$ | OH | H | 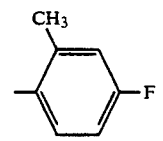 |
| H | H | H | OH | H | 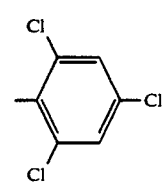 |

TABLE 1-continued
| R¹ | R² | R³ | R⁴ | R⁵ | Ar |
|---|---|---|---|---|---|
| H | H | H | Cl | H | 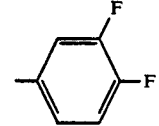 |
| H | H | H | Cl | H | 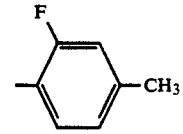 |
| H | H | H | Br | H | 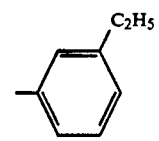 |
| Cl | H | H | F | H | 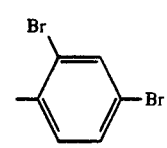 |
| Cl | H | H | H | $-C_3H_7$-n | 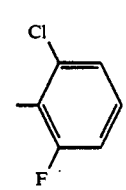 |
| Cl | H | H | H | H | 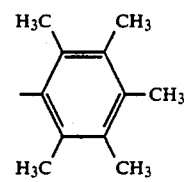 |
| Cl | H | H | H | H | 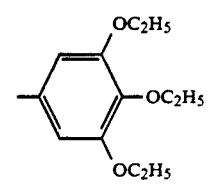 |
| Br | H | H | H | $CH_3$ | 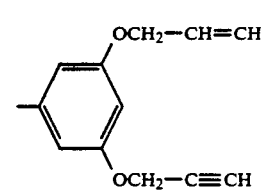 |
| Br | H | H | $CH_3O$ | H | 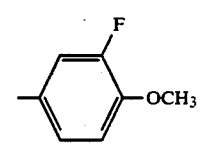 |
| $CH_3O-$ | H | H | H | H | 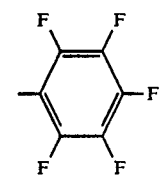 |

TABLE 1-continued
| $R^1$ | $R^2$ | $R^3$ | $R^4$ | $R^5$ | Ar |
|---|---|---|---|---|---|
| $CH_3O-$ | H | H | H | H | 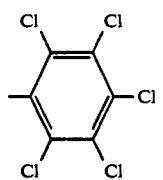 pentachlorophenyl |
| $C_2H_5O-$ | H | H | H | H | 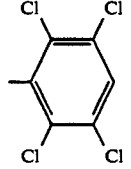 pentachlorophenyl |
| $n-C_3H_7O-$ | H | H | OH | OH | 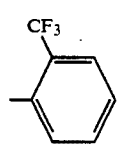 2-(CF$_3$)phenyl |
| $i-C_3H_7O-$ | H | H | SH | H | 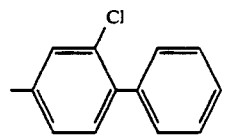 2-chlorobiphenyl |
| $-CF_3$ | H | H | $NH_2$ | H | 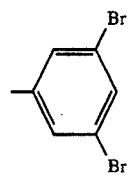 3,5-dibromophenyl |
| $CH_3S-$ | H | H | H | $-C_2H_5$ | 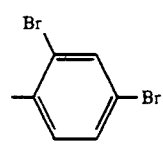 2,4-dibromophenyl |
| $CH_3S-$ | H | H | $CH_3$ | H | 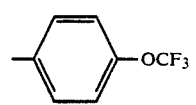 4-(OCF$_3$)phenyl |
| $C_2H_5S-$ | H | H | H | H | 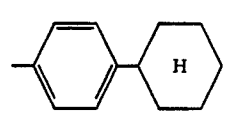 4-cyclohexylphenyl |
| $C_2H_5S-$ | H | H | H | H | 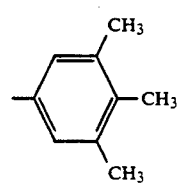 2,3,5-trimethylphenyl |
| $(CH_3)_2N-$ | H | H | H | H | 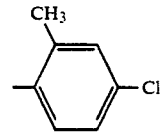 4-chloro-2-methylphenyl |

TABLE 1-continued

| R¹ | R² | R³ | R⁴ | R⁵ | Ar |
|---|---|---|---|---|---|
| (C₂H₅)₂N— | H | H | H | H | 3,5-bis(SCH₃)-phenyl |
| —CCl₃ | H | H | Cl | H | 3,4-bis(OCH₃)-phenyl |
| —CHF₂ | H | H | H | H | 3-F-phenyl |
| C₆H₅O— | H | H | H | H | 3-I-phenyl |
| C₆H₅O— | H | H | H | CH₃ | 4-(CH=CH₂)-phenyl |
| C₆H₅O— | H | H | OH | H | 3-C₂H₅, 4-C₂H₅-phenyl |
| C₆H₅S— | H | H | OH | H | 4-(C₄H₉-n)-phenyl |
| C₆H₅S— | H | H | Cl | H | 3,4-bis(OCF₃)-phenyl |
| C₆H₅S— | H | H | CH₃O— | H | 3-SCF₃-phenyl |
| C₆H₅CH₂O— | H | H | OH | C₂H₅ | 3,5-diF-4-SCClF₂-phenyl |
| C₆H₅CH₂O— | H | H | CH₃O— | H | phenyl |

TABLE 1-continued

| R¹ | R² | R³ | R⁴ | R⁵ | Ar |
|---|---|---|---|---|---|
| C₆H₅-CH₂O— | H | H | CH₃S— | H | 2-Br, 3-OC₂H₅-phenyl |
| C₆H₅-CH₂S— | H | H | Cl | H | 3-F, 5-Cl-phenyl |
| C₆H₅-CH₂S— | H | H | F | H | phenyl |
| C₆H₅-CH₂S— | H | H | H | H | 2,3-(OH)₂, 4-CH₃-phenyl |
| C₆H₅-O— | H | H | H | H | 4-SH-phenyl |
| F | H | H | H | n-C₃H₇ | 2-NH₂, 3-CH₃-phenyl |
| F | H | H | CH₃ | H | 4-N(CH₃)₂-phenyl |
| Cl | H | H | C₂H₅O— | H | 3-CN, 5-Cl-phenyl |
| Br | H | H | CH₂=CH—CH₂O— | H | 2-Cl, 4-NHNH₂-phenyl |
| H | H | H | i-C₃H₇O— | H | 4-OC₄H₉-t-phenyl |

TABLE 1-continued
| R¹ | R² | R³ | R⁴ | R⁵ | Ar |
|---|---|---|---|---|---|
| 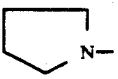 | H | H | H | H | 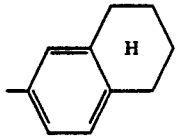 |
| 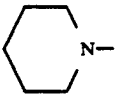 | H | H | H | CH₃ | 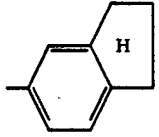 |
| H | | 4,5-(CH₂)₄— | H | H | 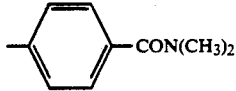—CON(CH₃)₂ |
| H | H | 3-CHCl₂ | CH₃ | H | 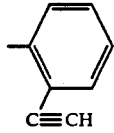 |
| 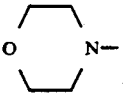 | H | H | H | C₂H₅ | 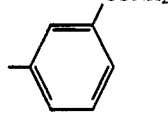 |
| H | 3-CHF₂ | H | CH₃S— | H |  |
| 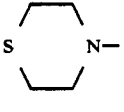 | | 3,4-(CH₂)₄— | CH₃O— | H | 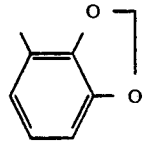 |
| 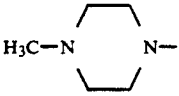 | H | H | C₂H₅S— | H | 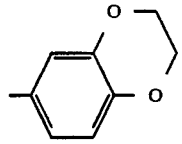 |
| H | 4-C₂H₅ | H | i-C₃H₇S— | H | 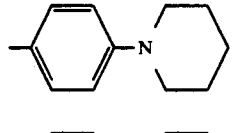 |
| H | | 4,5-(CH₂)₃ | H | CH₃ | 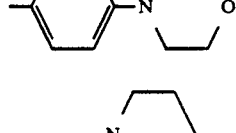 |
| H | 5-CH₃ | 3-CH₃ | H | H | 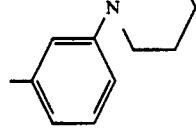 |

TABLE 1-continued

| R¹ | R² | R³ | R⁴ | R⁵ | Ar |
|---|---|---|---|---|---|
| CH₃-CH(—)-CH₂-N(—)-CH₂-CH(CH₃)-O (2,6-dimethylmorpholino) | H | H | CH₃ | H | 2-(NHN(CH₃)₂)-phenyl |
| 1-pyrrolidinyl (N-methyl) | H | 3-CH₃ | t-C₄H₉S— | H | 2-(4-methylpiperazin-1-yl)-phenyl with ortho-CH₃ |
| (C₂H₅)₂N— | H | H | F | H | 2,3,4,5-tetrahydro-1H-1,5-benzodiazepin-... with CH₃ |
| H | 5-F | 3-F | CH₃ | CH₃ | 3-(CO₂CH₃)-phenyl |
| piperidin-1-yl | H | n-C₃H₇ | Br | H | 3-(NHNH-C₆H₅)-phenyl |

If, for example, 4-chloro-2-(2-pyridyl)-6-(4-fluorophenyl)-pyrimidine is used as starting substance and hydrogen and palladium/carbon as catalyst, process (A) according to the invention may be described by the following equation

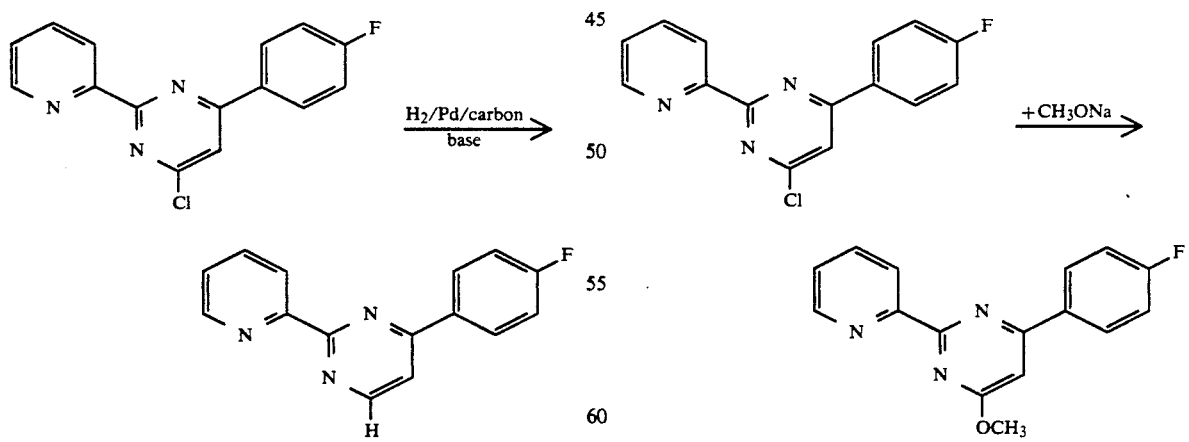

If, for example, 4-chloro-2-(2-pyridyl)-6-(4-fluorophenyl)-pyrimidine and sodium methanolate are used as starting substances, process (B) according to the invention can be described by the following equation:

If, for example, 4-chloro-2-(2-pyridyl)-6-(4-fluorophenyl)-pyrimidine and diethyl malonate are used, process (C) according to the invention may be represented by the following equation:

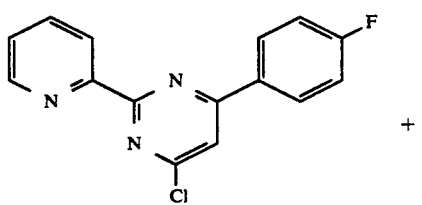

+

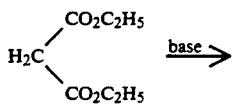

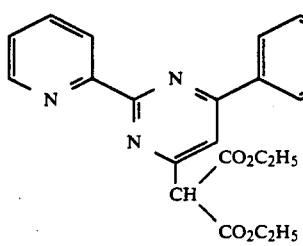

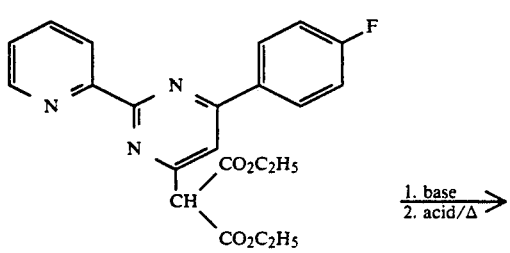

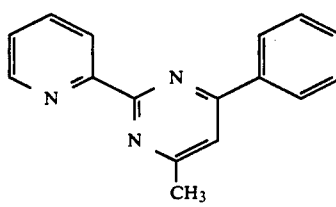

If, for example, 2-pyridinyl-amidine hydrochloride and 1-(4-cyclohexyl-phenyl)-3-dimethylaminopropen-1-one and sodium methylate are used as starting substances, process (D-α) according to the invention may be represented by the following equation:

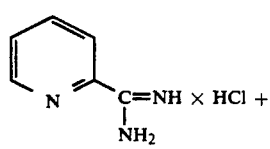

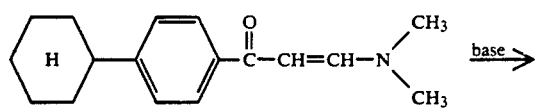

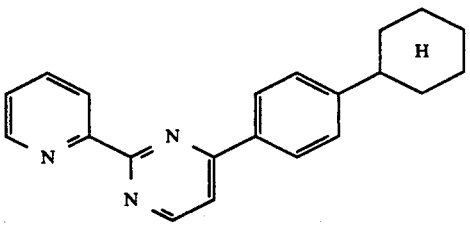

If, for example, 2-pyridinyl-amidine hydrochloride and 1-phenyl-3,3-dimethoxy-propan-1-one are used, process (D-β) according to the invention may be described by the following equation:

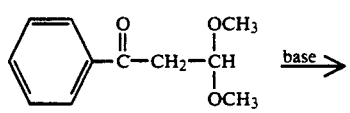

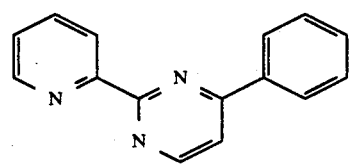

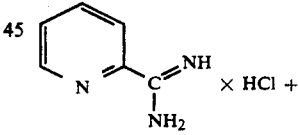

If, for example, 2-pyridinyl-amidine hydrochloride and 1-phenyl-1,3-butanedione are used as starting substances, process (D-γ) according to the invention may be described by the following equation:

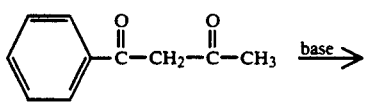

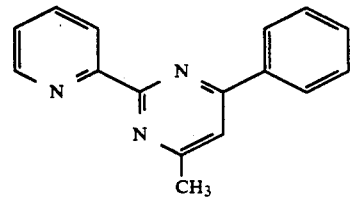

If, for example, 2-pyridinyl-amidine hydrochloride and 1,1,3,3-tetramethoxypropyl-benzene are used, process (D-δ) according to the invention may be described by the following equation:

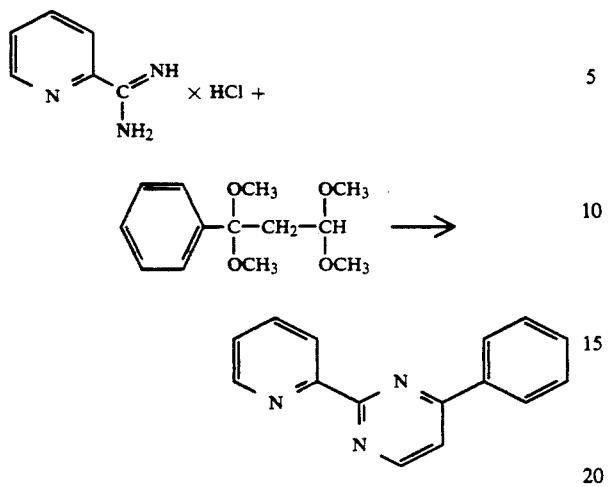

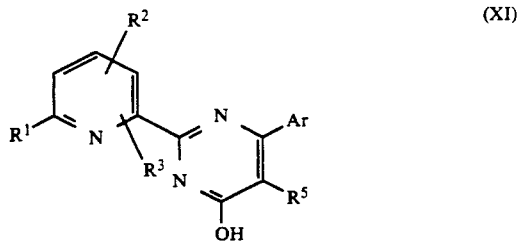

in which
R[1], R[2], R[3], R[5] and Ar have the abovementioned meanings, and the resulting compounds of the formula (XI) are halogenated with a halogenation reagent, such as, for example, thionyl chloride, phosgene, phosphoryl chloride, phosphorus pentachloride, phosphoryl bromide or phosphorus tribromide, at temperatures between 50° C. and 150° C., if appropriate after they have been isolated and if appropriate in the presence of a diluent, such as, for example, benzene, toluene or chlorobenzene (cf. EP-OS (European Published Specification) 259,139 and EP-OS (European Published Specification) 270,362).

Formula (II) provides a general definition of the halogen-substituted pyridinylpyrimidine derivatives required as starting substances for carrying out processes (A), (B) and (C) according to the invention. In this formula (II), R[1], R[2], R[3], R[5], Ar and X represent those radicals which have already been mentioned in connection with the description of the substances of the formula (I) according to the invention as being preferred for these substituents.

The compounds of the formula (II) are new. However, they can obtained in analogous manner by known processes, for example by a process in which picolineamine derivatives of the formula (V)

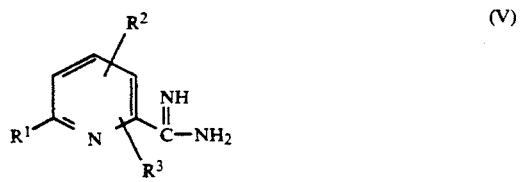

in which
R[1], R[2] and R[3] have the abovementioned meanings, their acid addition salts,
are cyclized with benzoyl acetic ester derivatives of the formula (X)

in which
Ar and R[5] have the abovementioned meanings and
R[9] represents methyl or ethyl, at temperatures of from 50° to 150° C., if appropriate in the presence of a diluent, such as, for example, methanol, ethanol, dioxane, tetrahydrofuran, pyridine, N,N-dimethylformamide, water or a mixture of water and the diluents mentioned, and if appropriate in the presence of a base, such as, for example, sodium hydroxide, potassium hydroxide, potassium carbonate, sodium methanolate, potassium methanolate, triethylamine or N,N-diethylaniline, to give the likewise new compounds of the formula (XI)

The picolineamine derivatives of the formula (V) or their acid addition salts are known in some cases and/or can be prepared in analogy to known processes (cf. EP-OS (European Published Specification) 259,139 and EP-OS (European Published Specification) 270,362).

Formula (III) provides a general definition of the compounds furthermore required as starting substances for carrying out process (B) according to the invention. In this formula (III), R[4-1] and M preferably represent those radicals which have already been mentioned in connection with the description of the substances of the formula (I) according to the invention as being preferred for these substituents.

The compounds of the formula (III) are generally known compounds of organic chemistry.

Formula (IV) provides a general definition of the diester derivatives furthermore required as starting substances for carrying out process (C) according to the invention. In this formula (IV), R[4-2] and R[6] preferably represent those radicals which have already been mentioned in connection with the description of the substances of the formula (I) according to the invention as being preferred for these substituents.

The compounds of the formula (IV) are generally known compounds of organic chemistry.

Formula (VI) provides a general definition of the aryl ketones furthermore required as starting substances for carrying out process (D-α) according to the invention. In this formula (VI), R[4-3], R[5] and Ar represent those radicals which have already been mentioned in connection with the description of the substances of the formula (I) according to the invention as being preferred for these substituents.

E preferably represents halogen, in particular chlorine, bromine or iodine, or represents dialkylamino, such as, for example, dimethylamino, or represents in each case optionally substituted alkylsulphonyloxy, alkoxysulphonyloxy or arylsulphonyloxy, such as, for example, methanesulphonyloxy, trifluoromethanesulphonyloxy, methoxysulphonyloxy, ethoxysulphonyloxy or p-toluenesulphonyloxy.

The compounds of the formulae (VI) are generally known compounds of organic chemistry.

Formula (VII) provides a general definition of the acetals furthermore required as starting substances for carrying out process (D-β) according to the invention. In this formula (VII), Ar, $A^{4-3}$ and $R^5$ represent those radicals which have already been mentioned in connection with the description of the substances of the formula (I) according to the invention as being preferred for these substituents.

$R^7$ preferably represents methyl or ethyl.

Formula (VIII) provides a general definition of the 1,3-dioxo derivatives furthermore required for carrying out process (D-γ) according to the invention. In this formula (VIII), Ar, $R^{4-3}$ and $R^5$ represent those radicals which have already been mentioned in connection with the description of the substances of the formula (I) according to the invention as being preferred for these substituents.

The compounds of the formula (VII) and (VIII) are generally known compounds of organic chemistry.

Formula (IX) provides a general definition of the diacetals furthermore required as starting substances for carrying out process (D-δ) according to the invention. In this formula (IX), Ar, $R^{4-3}$ represent those radicals which have already been mentioned in connection with the description of the substances of the formula (I) according to the invention as being preferred for these substituents.

$R^8$ preferably represents methyl or ethyl.

The compounds of the formula (IX) are generally known compounds of organic chemistry.

Process (A) according to the invention for the preparation of the new compounds of the formula (Ia) is preferably carried out using diluents. Diluents which are suitable for this purpose are virtually all inert organic solvents. These include benzene, toluene, xylene, tetrahydrofuran and dioxane, esters, such as methyl acetate and ethyl acetate, alcohols, such as methanol, ethanol and isopropanol, and also water. Preferably used diluents are water, methanol, ethanol, ethyl acetate and toluene, or mixtures of these diluents.

When carrying out process (A) according to the invention, the reaction temperatures can be varied within a substantial range. In general, the process is carried out at temperatures between 0° C. and +100° C., preferably at temperatures between +20 C and +50° C.

Process (A) according to the invention is preferably carried out using catalysts. Suitable catalysts are customary hydrogenation catalysts, such as, for example, Raney nickel, elementary platinum or palladium, but palladium/active carbon is preferably used.

Process (A) according to the invention is carried out in the presence of bases. Examples of suitable bases are alkali metal hydroxides, such as, for example, sodium hydroxide and potassium hydroxide, alkaline earth metal hydroxides, such as, for example, calcium hydroxide, alkali metal carbonates, alkali metal acetates and alkali metal alcoholates, such as sodium carbonate, potassium carbonate, sodium methylate, potassium methylate, sodium ethylate and potassium ethylate, ammonia, amines, such as diethylamine, or basic ion exchangers.

Process (A) according to the invention is generally carried out at a hydrogen pressure of 1 to 5 atmospheres, preferably at 1 to 3 atmospheres. For working up, the catalyst is filtered off, water is added to the reaction solution, and the mixture is extracted with an organic solvent. Further working-up is carried out by customary methods.

For carrying out process (A) according to the invention, 1 to 10 moles, preferably 1 to 5 moles, of hydrogen and 0.01 to 1 mole, preferably 0.01 to 0.1 mole, of catalyst are generally employed per mole of halogenated pyridinylpyrimidine derivative of the formula (II).

Process (B) according to the invention for the preparation of the new compounds of the formula (Ib) is preferably carried out using diluents. Suitable diluents for this purpose are virtually all inert organic solvents. These include aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether and dibutyl ether, glycol dimethyl ether and diglycol dimethyl ether, tetrahydrofuran and dioxane, alcohols, such as methanol, ethanol or isopropanol. Preferably used diluents are ethers, such as diethyl ether, dioxane and tetrahydrofuran, and alcohols such as methanol and ethanol, or mixtures of these diluents.

When carrying out process (B) according to the invention, the reaction temperatures can be varied within a substantial range. In general, the process is carried out at temperatures between 0° C. and +150° C., preferably at temperatures between +10° C. and +120° C.

Process (B) according to the invention is carried out in the presence of bases. Preferably used bases are alkali metal hydroxides, such as sodium hydroxide or potassium hydroxide, or organic bases, such as sodium methanolate, triethylamine or pyridine.

For carrying out process (B) according to the invention, 1 to 3 moles, preferably 1 to 1.5 moles, of compound of the formula (III) are generally employed per mole of halogen-substituted pyridinylpyrimidine derivative of the formula (II).

For carrying out process (B) according to the invention, the reaction mixture is stirred for several hours at the required temperature. Working-up is carried out by customary methods, and, if appropriate, the product is subsequently purified by chromatography.

Process (C) according to the invention for the preparation of the new compounds of the formula (Ic) is preferably carried out using diluents. Suitable diluents for this purpose are virtually all inert organic solvents. These preferably include aliphatic and aromatic, optionally halogenated hydrocarbons, such as benzene, toluene, xylene, methylene chloride, ethylene chloride, chloroform, carbon tetrachloride, chlorobenzene and o-dichlorobenzene, ethers, such as diethyl ether and dibutyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, dimethyl sulphoxide and sulpholane, and mixtures of these diluents.

When carrying out the first reaction step of process (C) according to the invention, the reaction temperatures can be varied within a substantial range. In general, the process is carried out at temperatures between −10° C. and +180° C., preferably at temperatures between 0° C. and +150 C.

The first reaction step of process (C) according to the invention is carried out in the presence of bases. Preferably used bases are alkali metal hydrides, such as, for example, sodium hydride, alkyllithium, such as n-butyllithium, lithiumdialkylamides, such as, for example, lithium diisopropylamide (LDA), alkali metal alcoholates, such as, for example, sodium methanolate and sodium ethanolate, and metal hydroxides, such as, for example, sodium hydroxide.

For carrying out the first reaction step of process (C) according to the invention, 0.5 to 2 moles, preferably 1 to 1.5 mole, of diester derivative of the formula (IV) and 1 to 3 moles, preferably 1 to 2 moles, of base are generally employed per mole of halogen-substituted pyridinylpyrimidine derivative of the formula (II).

When carrying out the second reaction step of process (C) according to the invention, the reaction temperatures can be varied within a substantial range. In general, the process is carried out at temperatures between 0° C. and +150° C., preferably at temperatures between +10° C. and +100° C.

The second reaction step of process (C) according to the invention is carried out in the presence of bases. Preferably used bases are alkali metal hydroxides, such as, for example, sodium hydroxide, and alkali metal carbonates, such as, for example, sodium carbonate.

For carrying out the second reaction step of process (C) according to the invention, 1 to 6 moles, preferably 2.1 to 2.5 moles, of base are generally employed per mole of halogen-substituted pyridinyl-pyrimidine derivative of the formula (II) used.

When carrying out the decarboxylation reaction of process (C) according to the invention, the reaction temperatures can be varied within a substantial range. In general, the process is carried out at temperatures between 0° C. and +200° C., preferably at temperatures between +20° C. and +150° C.

The decarboxylation reaction of process (C) according to the invention is carried out in the presence of acids. Preferably used acids are inorganic acids, such as, for example, sulphuric acid or hydrochloric acid, and organic acids, such as, for example, acetic acid.

For carrying out the decarboxylation reaction of process (C) according to the invention, 1 to 10 moles, preferably 2.5 to 6 moles, of acid are generally employed per mole of halogen-substituted pyridinyl-pyrimidine of the formula (II) used.

Process (C) according to the invention is carried out by customary methods. For working-up, the reaction mixture is neutralized, concentrated and extracted. The product is purified by chromatography or recrystallization.

Process (D-α) according to the invention for the preparation of the new compounds of the formula (I-d) is preferably carried out using diluents. Suitable diluents for this purpose are virtually all inert organic solvents. These preferably include ethers, such as tetrahydrofuran and dioxane, amides, such as, for example, dimethylformamide, dimethylacetamide and pyridine, and alcohols, such as methanol and ethanol.

When carrying out process (D-α) according to the invention, the reaction temperatures can be varied within a substantial range. In general, the process is carried out at temperatures between 0° C. and +200° C., preferably at temperatures between +50° C. and +150° C.

Process (D-α) according to the invention is carried out in the presence of bases. Preferably used bases are metal alcoholates, such as, for example, sodium methanolate and sodium ethanolate, and organic bases, such as, for example, trimethylamine, triethylamine and N,N-diethylaniline.

The reaction is carried out and the product is worked up by customary methods by concentration under reduced pressure followed, if appropriate, by chromatographic purification.

For carrying out process (D-α) according to the invention, 1 to 3 moles, preferably 1 to 1.5 moles, of aryl ketone of the formula (VI) and 0.1 to 5 moles, preferably 0.1 to 2.5 moles, of base are generally employed per mole of picolineamidine derivative of the formula (V).

Process (D-β) according to the invention for the preparation of the new compounds of the formula (I-d) is preferably carried out using diluents. Suitable diluents for this purpose are ethers, such as tetrahydrofuran and dioxane, amides, such as, for example, dimethylformamide, dimethylacetamide and pyridine, water, or mixtures of the solvents mentioned.

When carrying out process (D-β) according to the invention, the reaction temperatures can be varied within a substantial range. In general, the process is carried out at temperatures between 0° C. and +200° C., preferably at temperatures between +50° C. and +150° C.

Process (D-β) according to the invention is carried out in the presence of bases. Preferably used bases are inorganic bases, such as sodium hydroxide, potassium hydroxide or potassium carbonate, or organic bases, such as sodium methanolate, triethylamine or N,N-diethylaniline.

For working-up after the reaction, inorganic salts which have formed are filtered off. The filtrate is concentrated and, if appropriate, purified by chromatography or recrystallization.

For carrying out process (D-β) according to the invention, 1 to 3 moles, preferably 1 to 1.5 moles, of acetal of the formula (VII) and 0.01 to 3, preferably 0.1 to 1 mole, of base are generally employed per mole of picolineamidine derivative of the formula (V).

Process (D-γ) according to the invention is carried out in the presence of bases. Preferably used bases are alkali metal alcoholates, such as, for example, sodium methanolate and sodium ethanolate, and organic bases, such as triethylamine and N,N-diethylaniline.

For carrying out process (D-γ) according to the invention, 1 to 3 moles, preferably 1 to 1.5 moles, of 1,3-dioxo derivative of the formula (VIII) and 0.1 to 5 moles, preferably 0.1 to 2.5 moles, of base are generally employed per mole of picolineamidine derivative of the formula (V).

For carrying out process (D-γ) according to the invention, the reaction mixture is stirred for several hours at the required temperature. The reaction product is worked up and isolated by customary methods.

Process (D) according to the invention, variant (δ), is preferably carried out in the absence of diluents. However, it is also possible to use one of the following diluents: aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether and dibutyl ether, glycol dimethyl ether and diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylformamide, dimethylacetamide and N-methyl-pyrrolidone, and dimethyl sulphoxide, tetramethylenesulphone and hexamethylphosphoric triamide.

When carrying out process (D) according to the invention, variant (δ), the reaction temperatures can be varied within a substantial range. In general, the process is carried out at temperatures between 0° C. and +200° C., preferably at temperatures between +50° C. and +150° C.

For carrying out process (D-δ) according to the invention, 1 to 5 moles, preferably 1 to 3 moles, of diacetal of the formula (IX) are generally employed per mole of picolineamidine derivative of the formula (V).

To carry out process (D-δ) according to the invention, the reaction mixture is stirred for several hours at the required temperature. Working-up is carried out by customary methods by concentration under reduced pressure followed by chromatographic purification.

The active compounds according to the invention have a powerful action against pests and can be employed in practice for combating undesired harmful organisms. The active substances are suitable for use as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation:

Pythium species, such as, for example, *Pythium ultimum;*

Phytophthora species, such as, for example, *Phytophthora infestans;*

Pseudoperonospora species, such as, for example, *Pseudoperonospora humuli* or *Pseudoperonospora cubensis;*

Plasmopara species, such as, for example, *Plasmopara viticola;*

Peronospora species, such as, for example, *Peronospora pisi* or *P. brassicae;*

Eyrsiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia, inaequalis;*

Pyrenophora species, such as, for example, *Pyrenophora teres* or *P. graminea* (conidia form: Drechslera, syn: Helminthosporium);

Cochliobolus species, such as, for example, *Cochliobolus sativus* (conidia form: Drechslera, syn: Helminthosporium);

Uromyces species, such as, for example, *Uromyces appendiulatus;*

Puccinia species, such as, for example, *Puccinia recondita;*

Tilletia species, such as, for example, *Tilletia caries;*

Ustilago species, such as, for example, *Ustilago nuda* or *Ustilago avenae;*

Pellicularia species, such as, for example, *Pellicularia sasakii;*

Pyricularia species, such as, for example, *Pyricularia cryzae;*

Fusarium species, such as, for example, *Fusarium culmorum;*

Botrytis species, such as, for example, *Botrytis cinerea;*

Septoria species, such as, for example, *Septoria nodorum;*

Leptosphaeria species, such as, for example, *Leptosphaeria nodorum;*

Cercospora species, such as, for example, *Cercospora canescens;*

Alternaria species, such as, for example, *Alternaria brassicae* and

Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

In this context, the active compounds according to the invention can be employed with particularly good success for combating diseases in fruit and vegetable growing, such as, for example, against the organism causing tomato rot (Phytophthora) and for protective treatment for example against apple scab (*Venturia inaequalis*), gray mold on beans (*Botrytis cinerea*), against *Erysiphe graminis* on wheat or barley, and against the organism causing leaf spot on barley (*Cochliobolus sativus*).

Some of the active compounds according to the invention furthermore show a good fungicidal action against *Septoria nodorum, Pyrenophora teres,* against *Fusarium culmorum, Fusarium nivaele* and against *Pyricularia oryzae* and *Pellicularia sasakii.* Some of the active compounds according to the invention also show a good and broad in-vitro action.

Depending on their particular physical and/or chemical properties, the active compounds can be converted into customary formulations, such as solutions, emulsions, suspensions, powders, foams, pastes, granules, aerosols, very fine capsules in polymeric substances and in coating compositions for seed, as well as ULV cold-mist and warm-mist formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenohydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds, such as fungicides, insecticides, acaricides and herbicides, as well as in mixtures with fertilizers and growth regulators.

The active compounds can be used as such or in the form of their formulations or the use forms prepared therefrom, such as ready-to-use solutions, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seeds of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02%, are required at the place of action.

The biological activity of the compounds according to the invention will be illustrated with reference to the use examples.

PREPARATION EXAMPLES

EXAMPLE 1

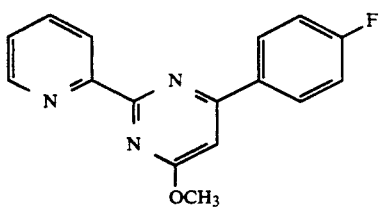

Process (B)

5.5 g (0.02 mol) of 4-chloro-2-(2-pyridyl)-6-(4-fluorophenyl)-pyrimidine are dissolved in 50 ml of dry methanol, 8.6 g of a 22% strength solution of sodium methylate in methanol (corresponds to 0.04 mol) are added, and the mixture is refluxed for 40 hours. After the solvent has been removed, the residue obtained is taken up in ethyl acetate and the mixture is washed twice with water and dried over sodium sulphate. After the solvent has been removed, 4.3 g (77% of theory) of 4-methoxy-2-(2-pyridyl)-6-(4-fluorophenyl)-pyrimidine of melting point 97°–98° C. are obtained.

EXAMPLE 2

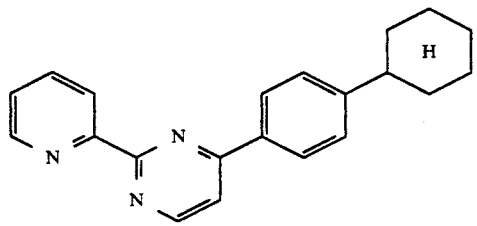

Process (D-α)

3.2 g (0.02 mol) of 2-pyridinyl-amidine hydrochloride and 5.1 g (0.02 mol) of 1-(4-cyclohexyl-phenyl)-3-dimethylamino-propen-one are dissolved in 50 ml of dry methanol, and 5.2 g of a 22% strength sodium methylate solution (corresponding to 0.024 mol) are added. The mixture is refluxed for 15 hours and the solution is subsequently neutralized with acetic acid. The solvents are distilled off under reduced pressure, and the residue is taken up in dichloromethane. The solution is washed with water and subsequently dried over sodium sulphate. After all volatile constituents have been removed under highly reduced pressure, 5.66 g (94% of theory) of 2-(2-pyridyl)-4-(4-cyclohexyl-phenyl)-pyrimidine are obtained as an oil.

$^1$H-NMR*):7.65; 8.95)

*) The $^1$H-NMR spectra were recorded in deuterochloroform (CDCl$_3$) with tetramethylsilane (TMS) as internal standard. The chemical shift is indicated as δ-value in ppm.

The pyridinylpyrimidine derivatives of the general formula (I) listed in Table 2 are obtained in a corresponding manner, analogously to the above-described processes (A), (B), (C), (D-α), (D-β), (D-γ) and (D-δ) and in accordance with the general preparation instructions:

TABLE 2
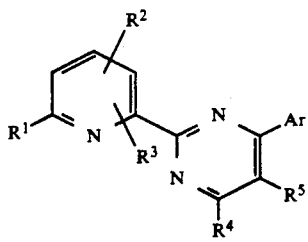
(I)
| Example No. | $R^1$ | $R^2$ | $R^3$ | $R^4$ | $R^5$ | Ar | Physical data |
|---|---|---|---|---|---|---|---|
| 3 | H | H | H | H | H | —C₆H₅ | $n_D^{20}$: 1.6605 |
| 4 | H | H | H | H | H | 4-Cl-C₆H₄— | m.p.: 109° C. |
| 5 | H | H | H | CF₃ | H | —C₆H₅ | m.p.: 75° C. |
| 6 | H | H | H | H | H | 2-CH₃-C₆H₄— | $n_D^{20}$: 1.6213 |
| 7 | H | H | H | H | H | 4-F-C₆H₄— | m.p.: 80° C. |
| 8 | H | H | H | CH₃ | H | —C₆H₅ | oil |
| 9 | H | H | H | H | H | 2-F-C₆H₄— | $n_D^{20}$: 1.6164 |
| 10 | H | H | H | H | H | 2-Br-C₆H₄— | m.p.: 45° C. |
| 11 | H | H | H | H | H | 3-CF₃-C₆H₄— | m.p.: 70° C. |
| 12 | H | H | H | H | CH₃ | 4-F-C₆H₄— | m.p.: 72° C. |

TABLE 2-continued
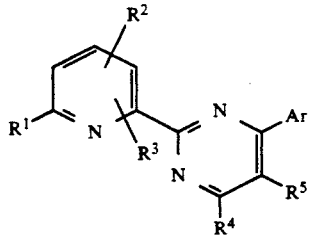
(I)
| Example No. | R¹ | R² | R³ | R⁴ | R⁵ | Ar | Physical data |
|---|---|---|---|---|---|---|---|
| 13 | H | H | H | H | H | 3-Br-C₆H₄ | oil |
| 14 | H | H | H | H | H | 4-OCH₃-C₆H₄ | oil |
| 15 | H | H | H | H | H | 4-Br-C₆H₄ | oil |
| 16 | H | H | H | H | H | 2,5-(OCH₃)₂-C₆H₃ | oil |
| 17 | H | H | H | H | H | 4-C₆H₅-C₆H₄ | m.p.: 141° C. |
| 18 | H | H | H | H | H | 3-CN-C₆H₄ | m.p.: 108° C. |
| 19 | H | H | H | H | H | 2,3,4-Cl₃-C₆H₂ | m.p.: 196° C. |
| 20 | H | H | H | H | H | 3,4-Cl₂-C₆H₃ | m.p.: 131° C. |
| 21 | H | H | H | H | H | 3-Br-4-F-C₆H₃ | oil |

TABLE 2-continued
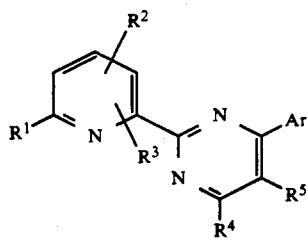
(I)
| Example No. | $R^1$ | $R^2$ | $R^3$ | $R^4$ | $R^5$ | Ar | Physical data |
|---|---|---|---|---|---|---|---|
| 22 | H | H | H | H | H | 3-methoxyphenyl | oil |
| 23 | H | H | H | H | H | 2-methoxyphenyl | oil |
| 24 | H | H | H | H | H | 2-chlorophenyl | m.p.: 100° C. |
| 25 | H | H | H | H | H | 4-methylphenyl | m.p.: 137° C. |
| 26 | H | H | H | H | H | 2-hydroxyphenyl | m.p.: 123° C. |
| 27 | H | H | H | H | H | 2,5-dimethylphenyl | oil |
| 28 | H | H | H | H | H | 2,4-dichlorophenyl | m.p.: 152° C. |
| 29 | H | H | H | H | $-C_2H_5$ | phenyl | oil |
| 30 | H | H | H | H | H | 3-methylphenyl | oil |

TABLE 2-continued
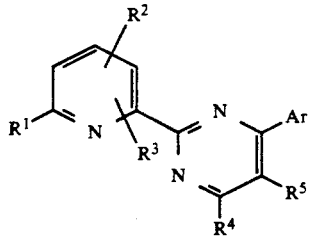
(I)
| Example No. | $R^1$ | $R^2$ | $R^3$ | $R^4$ | $R^5$ | Ar | Physical data |
|---|---|---|---|---|---|---|---|
| 31 | H | H | H | H | H | 3-Cl-C6H4 | oil |
| 32 | H | H | H | H | CH3 | C6H5 | oil |
| 33 | H | H | H | H | CH3 | 4-CH3-C6H4 | oil |
| 34 | H | H | H | H | H | 4-PhO-C6H4 | oil |
| 35 | H | H | H | H | H | 2,4-F2-C6H3 | m.p.: 117° C. |
| 36 | H | H | H | H | H | 3-F-4-OCH3-C6H3 | m.p.: 98° C. |
| 37 | H | H | H | H | H | 2,6-Cl2-C6H3 | oil |
| 38 | H | H | H | CH3 | H | 4-F-C6H4 | m.p.: 80° C. |
| 39 | H | H | H | CH3 | H | 3,4-F2-C6H3 | m.p.: 124° C. |

TABLE 2-continued
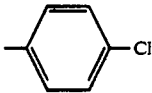
(I)
| Example No. | $R^1$ | $R^2$ | $R^3$ | $R^4$ | $R^5$ | Ar | Physical data |
|---|---|---|---|---|---|---|---|
| 40 | H | H | H | H | $CH_3$ | 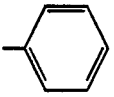 | m.p.: 122° C. |
| 41 | H | H | H | H | $-C_3H_7$ | 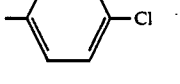 | m.p.: 101° C. |
| 42 | H | 5-$CF_3$ | H | H | H | 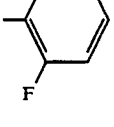 | m.p.: 162° C. |
| 43 | H | 5-$CF_3$ | H | H | H | 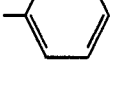 | m.p.: 118° C. |
| 44 | H | H | H | $-OCH_3$ | H | 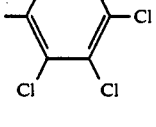 | m.p.: 94° C. |
| 45 | F | 5-$CF_3$ | H | H | H | 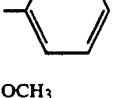 | m.p.: 201° C. |
| 46 | H | H | H | $-SCH_3$ | H | 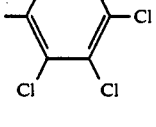 | m.p.: 94° C. |
| 47 | H | 5-$CF_3$ | H | H | H | 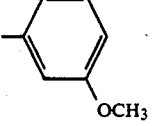 | m.p.: 133° C. |
| 48 | H | H | H | H | H | 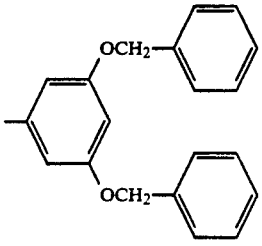 | m.p.: 40° C. |

TABLE 2-continued
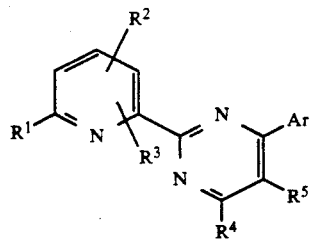
(I)
| Example No. | R¹ | R² | R³ | R⁴ | R⁵ | Ar | Physical data |
|---|---|---|---|---|---|---|---|
| 49 | H | H | H | —SCH₃ | H | 4-F-C₆H₄ | m.p.: 96° C. decomp. |
| 50 | H | H | H | —SC₂H₅ | H | 4-F-C₆H₄ | oil |
| 51 | H | 5-CF₃ | H | H | H | 4-CH₃-C₆H₄ | m.p. 141° C. |
| 52 | H | H | H | H | H | 4-CF₃-C₆H₄ | m.p.: 135° C. |
| 53 | H | H | H | H | H | 4-C₂H₅-C₆H₄ | m.p.: 85° C. |
| 54 | H | H | H | H | H | 3-C₂H₅-C₆H₄ | oil |
| 55 | H | H | H | H | CH₃ | 2-F-C₆H₄ | m.p. 124° C. |
| 56 | H | H | H | —SC₂H₅ | H | C₆H₅ | oil |
| 57 | H | H | H | —SC₄H₉-t | H | C₆H₅ | m.p.: 90° C. |
| 58 | H | H | H | H | H | 4-Cl-3-CH₃-C₆H₃ | oil |

TABLE 2-continued
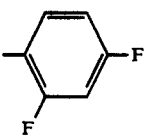
(I)
| Example No. | R¹ | R² | R³ | R⁴ | R⁵ | Ar | Physical data |
|---|---|---|---|---|---|---|---|
| 59 | H | H | H | H | H | 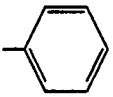 2,4-difluorophenyl | oil |
| 60 | H | H | H | —SC$_3$H$_7$-i | H | 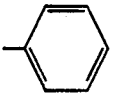 phenyl | oil |
| 61 | H | H | H | —SC$_3$H$_7$-n | H | phenyl | m.p.: 51° C. |
| 62 | H | H | H | H | H | 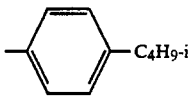 4-(i-C$_4$H$_9$)phenyl | Oil |
| 63 | H | H | H | H | H | 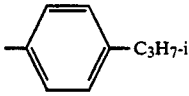 4-(i-C$_3$H$_7$)phenyl | m.p.: 70° C. |
| 64 | H | H | H | H | H | 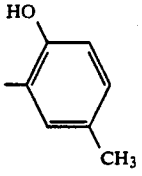 3-HO-5-CH$_3$-phenyl | m.p.: 158° C. |
| 65 | H | H | H | SC$_4$H$_9$-n | H | 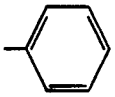 phenyl | m.p.: 72° C. |
| 66 | Br | H | H | H | H | 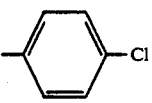 4-Cl-phenyl | m.p.: 158–160° C. |
| 67 | H | H | H | H | H | 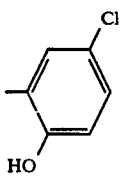 4-Cl-3-HO-phenyl | m.p.: 174° C. |

TABLE 2-continued
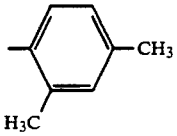
(I)
| Example No. | R¹ | R² | R³ | R⁴ | R⁵ | Ar | Physical data |
|---|---|---|---|---|---|---|---|
| 68 | H | H | H | H | H | 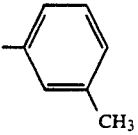 | ¹H-NMR* δ = (9.0 d, 1H) |
| 69 | Br | H | H | H | H | 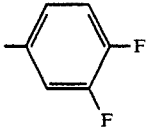 | m.p.: 96° C. |
| 70 | H | H | H | H | H | 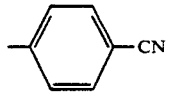 | m.p.: 112° C. |
| 71 | H | H | H | H | H | 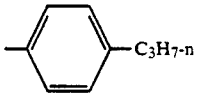 | m.p.: 114° C. |
| 72 | H | H | H | H | H | 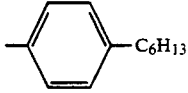 | m.p.: 86° C. |
| 73 | H | H | H | H | H | 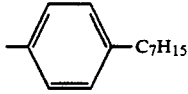 | ¹H-NMR* δ = 7,7 (d, 1H) |
| 74 | H | H | H | H | H | 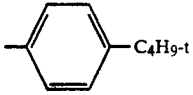 | ¹H-NMR* δ = 7,7 (d, 1H) |
| 75 | H | H | H | H | H | 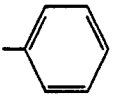 | m.p.: 93° C. |
| 76 | H | H | H | OC₂H₅ | H |  | m.p.: 52° C. |
| 77 | H | H | H | H | H | 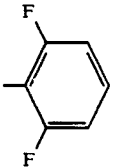 | ¹H-NMR* δ = 7,5 (m, 1H) |

TABLE 2-continued
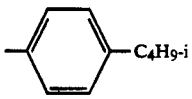
(I)
| Example No. | R¹ | R² | R³ | R⁴ | R⁵ | Ar | Physical data |
|---|---|---|---|---|---|---|---|
| 78 | H | CH₃ | H | H | H | 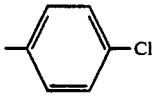 —C₄H₉-i | ¹H-NMR* δ = 7,65 (d, 1H) |
| 79 | H | CH₃ | H | H | H | 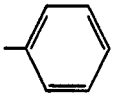 —Cl | m.p.: 100° C. |
| 80 | H | 4-CH₃ | H | —OH | H | 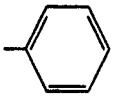 | m.p. 159° C. |
| 81 | H | 4-CH₃ | H | —SC₂H₅ | H | 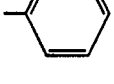 | ¹H-NMR (CDCl₃)* α = 2,5 (S, 3H) ppm |
| 82 | H | 4-CH₃ | H | —Cl | H | 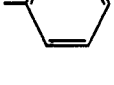 | m.p. 150° C. |
| 83 | H | H | H | —OC₃H₇-n | H | 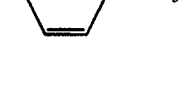 | m.p. >250° C. |
| 84 | H | H | H | H | H |  —OCF₃ | m.p. 90° C. |
| 85 | H | H | H | H | H | 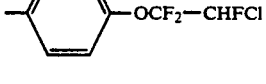 —OCF₂—CHF₂ | m.p. 98° C. |
| 86 | H | H | H | H | H | 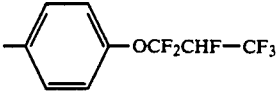 —OCF₂—CHFCl | m.p. 109° C. |
| 87 | H | H | H | H | H | —OCF₂CHF—CF₃ | ¹H-NMR (CDCl₃)* δ = 7,7 (δ, 1H, J=6H₂) |

TABLE 2-continued

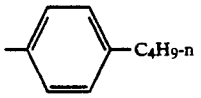

| Example No. | R¹ | R² | R³ | R⁴ | R⁵ | Ar | Physical data |
|---|---|---|---|---|---|---|---|
| 88 | H | H | H | H | H | | ¹H-NMR (CDCl₃)* α = 7,7 (α, 1H, J=6H$_z$) |

*The ¹H-NMR spectra were recorded deuterochloroform (CDCl₃) with tetramethylsilane (TMS) as internal standard. The value indicated is the chemical shift as the δ-value in ppm.

PREPARATION OF THE STARTING COMPOUNDS

EXAMPLE XI-1

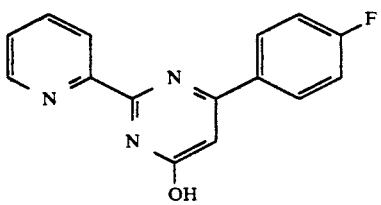

4.2 g (0.18 mol) of sodium are dissolved in 230 ml of dry ethanol and 22.8 g (0.145 mol) of 2-pyridinyl-amidine hydrochloride and 32.4 g (0.165 mol) of methyl 4-fluorobenzoylacetate are added. The mixture is refluxed for 1 hour, then neutralized with concentrated acetic acid and concentrated under reduced pressure. The residue obtained is recrystallized from ethanol.

18.3 g (46% of theory) of 4-hydroxy-2-(2-pyridyl)-6-(4-fluorophenyl)-pyrimidine of melting point 197°–198° C. are obtained.

The compounds of the formula (XI) listed in Table 3 are obtained in a corresponding manner and following the general preparation instructions:

TABLE 3

| Example No. | R¹ | R² | R³ | R⁵ | Ar | Physical constants |
|---|---|---|---|---|---|---|
| XI-2 | H | H | H | H | phenyl | m.p.: 250° C. |
| XI-3 | H | H | H | H | 4-OCH₃-phenyl | m.p.: 180° C. |
| XI-4 | H | H | H | H | 3-NO₂-phenyl | m.p.: 218° C. |

TABLE 3-continued (XI) structure with $R^1$, $R^2$, $R^3$, $R^5$, Ar, OH substituents on pyridyl-pyrimidine

| Example No. | $R^1$ | $R^2$ | $R^3$ | $R^5$ | Ar | Physical constants |
|---|---|---|---|---|---|---|
| XI-5 | H | H | H | H | 2-fluorophenyl | m.p.: 143° C. |
| XI-6 | H | H | H | H | 4-nitrophenyl | m.p.: >250° C. |
| XI-7 | H | 5-CF$_3$ | H | H | phenyl | m.p.: 157° C. |
| XI-8 | H | 5-CF$_3$ | H | H | 2-fluorophenyl | m.p.: 166° C. |

EXAMPLE II-1

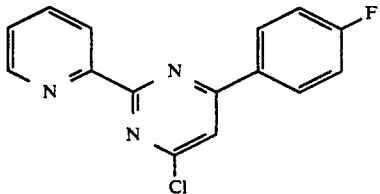

5.3 g (0.02 mol) of 4-hydroxy-2-(2-pyridyl)-6-(4-fluorophenyl)-pyrimidine and 6.1 g (0.04 mol) of phosphorus oxychloride are refluxed for 2 hours. The residue obtained is filtered off with suction and washed with petroleum ether.

4.9 g (98% of theory) of 4-chloro-2-(2-pyridinyl)-6-(4-fluorophenyl)-pyrimidine of melting point 156° C. are obtained.

The compounds of the formula (II) listed in Table 4 are obtained in a corresponding manner and following the general preparation instructions:

TABLE 4

(II) structure with $R^1$, $R^2$, $R^3$, $R^5$, X, Ar substituents

| Example No. | $R^1$ | $R^2$ | $R^3$ | $R^5$ | X | Ar | Physical constants |
|---|---|---|---|---|---|---|---|
| II-2 | H | H | H | H | Cl | 3-nitrophenyl | m.p.: 157° C. decomp. |

TABLE 4-continued

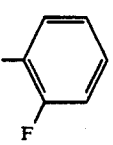

| Example No. | R¹ | R² | R³ | R⁵ | X | Ar | Physical constants |
|---|---|---|---|---|---|---|---|
| II-3 | H | H | H | H | Cl | 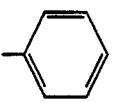 | m.p.: 170° C. decomp. |
| II-4 | H | H | H | H | Cl | 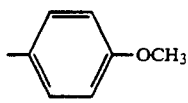 | m.p.: 152° C. |
| II-5 | H | H | H | H | Cl | 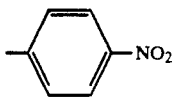 —OCH₃ | m.p.: 134° C. decomp. |
| II-6 | H | H | H | H | Cl | 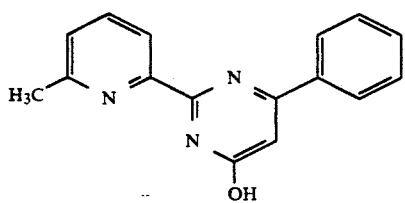 —NO₂ | m.p.: 125° C. decomp. |

USE EXAMPLES

In the following use examples, the compounds listed below are employed as comparison substances:

(A) 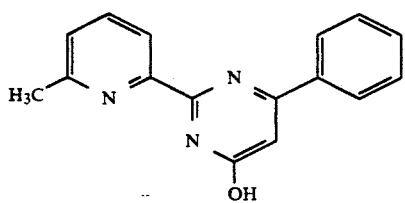

(B) 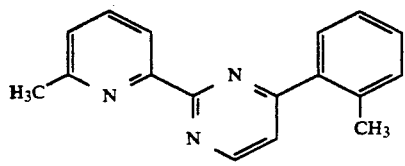

(disclosed in EP 0,270,362)

(C) 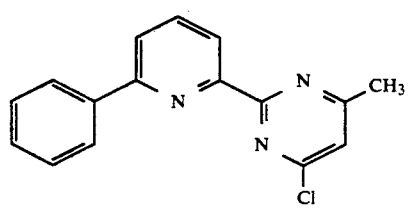

(disclosed in EP 0,259,139)

EXAMPLE A

Phytophthora Test (tomato)//curative

| Solvent: | 4.7 parts by weight of acetone |
|---|---|
| Emulsifier: | 0.3 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for curative activity, young plants are inoculated with an aqueous spore suspension of *Phytophthora infestans*. The plants remain in an incubation cabin at 20° C. and 100% relative atmospheric humidity for 7 hours. After a short drying-off time, the plants are sprayed with the preparation of active compound until dripping wet.

The plants are placed in an incubation cabin at 100% relative atmospheric humidity and at about 20° C.

Evaluation is carried out 3 days after the inoculation.

In this test, a clearly superior activity compared with the prior art is shown, for example, by the compounds according to the following Preparation Examples: 12, 17, 19, 20, 22, 23, 24 and 25.

EXAMPLE B

Venturia test (apple)/protective

| Solvent: | 4.7 parts by weight of acetone |

-continued

| | |
|---|---|
| Emulsifier: | 0.3 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (*Venturia inaequalis*) and then remain in an incubation cabin at 20° C. and 100% relative atmospheric humidity for 1 day.

The plants are then placed in a greenhouse at 20° C. and a relative atmospheric humidity of about 70%.

Evaluation is carried out 12 days after the inoculation.

In this test, a clearly superior activity compared with the prior art is shown, for example, by the compounds according to the following Preparation Examples: 11, 12 and XI-5.

EXAMPLE C

Botrytis test (bean)/protective

| | |
|---|---|
| Solvent: | 4.7 parts by weight of acetone |
| Emulsifier: | 0.3 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, 2 small pieces of agar covered with *Botrytis cinerea* are placed on each leaf. The inoculated plants are placed in a darkened humid chamber at 20° C. 3 days after the inoculation, the size of the infected spots on the leaves is evaluated.

In this test, a clearly superior activity compared with the prior art is shown, for example, by the compound according to Preparation Example 26.

EXAMPLE D

Erysiphe test (barley)/protective

| | |
|---|---|
| Solvent: | 100 parts by weight of dimethylformamide |
| Emulsifier: | 0.25 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of *Erysiphe graminis* f.sp. hordei.

The plants are placed in a greenhouse at a temperature of about 20° C. and a relative atmospheric humidity of about 80%, in order to promote the development of mildew pustules.

Evaluation is carried out 7 days after the inoculation.

In this test, a clearly superior activity compared with the prior art is shown, for example, by the compounds according to the following Preparation Examples: 2, 3, 4, 7, 11, 26, 28, 30, 31, II-5 and II-6.

EXAMPLE E

Erysiphe test (wheat)/protective

| | |
|---|---|
| Solvent: | 100 parts by weight of dimethylformamide |
| Emulsifier: | 0.25 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of Erysiphe graminis f.sp. tritici.

The plants are placed in a greenhouse at a temperature of about 20° C. and a relative atmospheric humidity of about 80%, in order to promote the development of mildew pustules.

Evaluation is carried out 7 days after the inoculation.

In this test, a clearly superior activity compared with the prior art is shown, for example, by the compounds according to Preparation Examples 3 and II-5.

EXAMPLE F

Cochliobolus sativus test (barley)/protective

| | |
|---|---|
| Solvent: | 100 parts by weight of dimethylformamide |
| Emulsifier: | 0.25 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of *Cochliobolus sativus*. The plants remain in an incubation cabin at 20° C. and 100% relative atmospheric humidity for 48 hours.

The plants are placed in a greenhouse at a temperature of about 20° C. and a relative atmospheric humidity of about 80%.

Evaluation is carried out 7 days after the inoculation.

In this test, a clearly superior activity compared with the prior art is shown, for example, by the compounds according to the following Preparation Examples: 2, 3, 4, 25, 29, 30, 31 and II-1.

It will be understood that the specification and examples are illustrative but not limitative of the present invention and that other embodiments within the spirit and scope of the invention will suggest themselves to those skilled in the art.

We claim:

1. A pyridinylpyrimidine of the formula

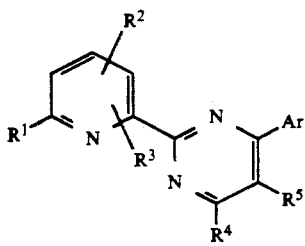 (I)

in which

R¹ represents hydrogen, halogen, in each case straight-chain or branched alkoxy or alkylthio each of which has 1 to 6 carbon atoms, or represents straight-chain or branched halogenoalkyl having 1 to 6 carbon atoms and 1 to 13 identical or different halogen atoms, or R¹ represents amino, alkylamino or dialkylamino each of which has 1 to 6 carbon atoms in the respective straight-chain or branched alkyl moieties, or R¹ represents a radical selected from

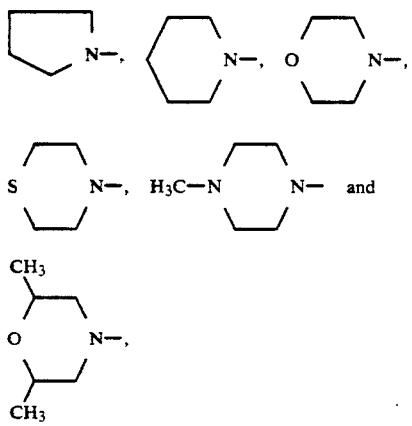

or

R¹ furthermore represents phenoxy or phenylthio, each of which is optionally monosubstituted, disubstituted or trisubstituted by identical or different substituents selected from the group consisting of halogen, cyano, nitro, alkyl, alkoxy or alkylthio each of which has 1 or 2 carbon atoms, and also halogenoalkyl, halogenoalkoxy or halogenoalkylthio each of which has 1 or 2 carbon atoms and each of which has 1 to 5 fluorine plus chlorine atoms, or R¹ represents phenylalkoxy or phenylalkylthio each of which has 1 to 4 carbon atoms in the respective straight-chain or branched alkyl moiety and each of which is optionally monosubstituted, disubstituted or trisubstituted on the phenyl moiety by identical or different substituents selected from the group consisting of halogen, cyano, nitro, alkyl, alkoxy or alkylthio each of which has 1 or 2 carbon atoms, and also halogenalkyl, halogenoalkoxy or halogenalkylthio each of which has 1 or 2 carbon atoms and each of which has 1 to 5 fluorine plus chlorine atoms.

R² and R³ are independent of one another and identical or different and in each case represent hydrogen, halogen, straight-chain or branched alkyl having 1 to 6 carbon atoms, or represents straight-chain or branched halogenoalkyl having 1 to 6 carbon atoms and 1 to 13 identical or different halogen atoms, or represents in each case straight-chain or branched alkoxy or alkylthio each of which has 1 to 6 carbon atoms, or represents straight-chain or branched alkoxycarbonyl having 1 to 6 carbon atoms in the alkoxy moiety, or R² and R³ together represent an alkylene chain which has 3 to 5 carbon atoms and which is linked via the ring positions 3 and 4 or 4 and 5, R⁴ represents hydrogen; halogen; straight-chain or branched alkyl having 1 to 6 carbon atoms; straight-chain or branched halogenoalkyl having 1 to 6 carbon atoms and 1 to 13 identical or different halogen atoms; hydroxyl; mercapto; straight-chain or branched alkoxy or alkylthio each of which has 1 to 6 carbon atoms; amino; alkylamino or dialkylamino each of which has 1 to 6 carbon atoms in the respective straight-chain or branched alkyl moieties, or R⁴ is represents a radial selected from

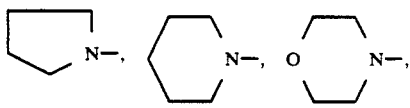

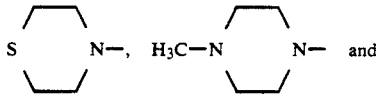

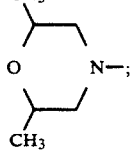

or

R⁴ represents in each case straight-chain or branched alkenyloxy or alkynyloxy each of which has 2 to 6 carbon atoms.

R⁵ represents hydrogen or straight-chain or branched alkyl having 1 to 6 carbon atoms, and Ar represents phenyl which is optionally monosubstituted, disubstituted or trisubstituted by identical or different substituents selected from the group consisting of halogen, cyano, nitro, hydroxyl, amino, mercapto, straight-chain or branched alkyl having 1 to 6 carbon atoms, straight-chain or branched halogenalkyl having 1 to 6 carbon atoms and 1 to 13 identical or different halogen atoms, straight-chain or branched alkoxy or alkylthio each of which has 1 to 6 carbon atoms, straight-chain or branched halogenalkylthio or halogenoalkoxy each of which has 1 to 6 carbon atoms and each of which has 1 to 13 identical or different halogen atoms, straight-chain or branched alkenyl or alkynyl having 2 to 6 carbon atoms, straight-chain or branched alkenyloxy or alkylnyloxy having 2 to 6 carbon atoms, cycloalkyl having 3 to 8 carbon atoms, phenyl, phenoxy, phenylthio, and phenylalkylthio or phenylalkyloxy each of which has 1 to 4 carbon atoms in the straight-chain or branched alkyl moiety, with the exception of the compounds 4-phenyl-2-(2-pyridinyl) pyrimidine, 4-(methyl-phenyl)-2-(2-pyridinyl)-pyrimidine, 4-halo-6-phenyl-2-(2-pyridyl)- pyrimidines and 4-halo-6-(methyl-phenyl)-2-(2-pyridyl)-pyrimidines.

2. A pyridinylpyrimidine according to claim 1, in which $R^1$ represents hydrogen, fluorine, chlorine, bromine, is each case straight-chain or branched alkoxy or alkylthio each of which has 1 to 4 carbon atoms, or represents straight-chain or branched halogenalkyl having 1 to 4 carbon atoms and 1 to 9 fluorine plus chlorine atoms, or $R^1$ represents amino, alkylamino or dialkylamino each of which has 1 to 4 carbon atoms in the respective straight-chain or branched alkyl moieties, or $R^1$ represents a radical selected from

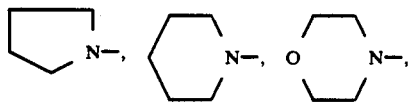

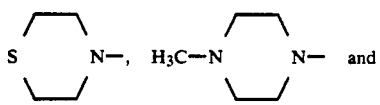

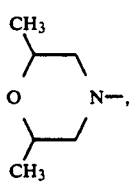

$R^1$ further represents phenoxy or phenylthio each of which is optionally monosubstituted or disubstituted by identical or different substituents selected from the group consisting of fluorine, chlorine, bromine, cyano, nitro, methyl, trifluoromethyl, methoxy, trifluoromethoxy, methylthio and trifluoromethylthio, or $R^1$ represents phenylalkoxy or phenylalkylthio each of which has 1 or 3 carbon atoms in the alkyl moiety and each of which is optionally monosubstituted or disubstituted on the phenyl moiety by identical or different substituents selected from the group consisting of fluorine, chlorine, bromine, cyano, nitro, methyl, trifluoromethyl, methoxy, trifluoromethoxy, methylthio and trifluoromethylthio, $R^2$ represents hydrogen, fluorine, chlorine or bromine, or represents straight-chain or branched alkyl, having 1 to 4 carbon atoms, straight-chain or branched halogenalkyl having 1 to 4 carbon atoms and 1 to 9 fluorine plus chlorine atoms, or represents in each case straight-chain or branched alkoxy or alkylthio having 1 to 4 carbon atoms, or represents straight-chain or branched alkoxycarbonyl having 1 to 4 carbon atoms in the alkoxy moiety, $R^3$ represents hydrogen, fluorine, chlorine, bromine or straight-chain or branched alkyl having 1 to 4 carbon atoms or $R^2$ and $R^3$ together represent an alkylene chain which has 3 or 4 carbon atoms and which is linked via the ring positions 3 and 4 or 4 and 5, $R^4$ represents hydrogen; fluorine, chlorine, bromine; straight-chain or branched alkyl having 1 to 4 carbon atoms; straight-chain or branched halogenalkyl having 1 to 4 carbon atoms and 1 to 9 fluorine plus chlorine atoms; hydroxyl; mercapto; straight-chain chain or branched alkoxy or alkylthio having 1 to 4 carbon atoms; amino; alkylamino or dialkylamino each of which has 1 to 4 carbon atoms in the respective straight-chain or branched alkyl moieties; or $R^4$ represents a radical selected from

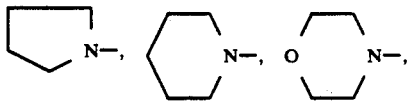

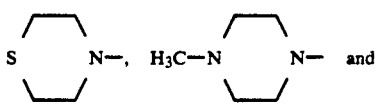

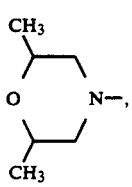

or $R^4$ represents straight-chain or branched alkenyloxy or alkinyloxy each of which has 3 or 4 carbon atoms, $R^5$ represents hydrogen or straight-chain or branched alkyl having 1 or 4 carbon atoms and Ar represents phenyl which is optionally monosubstituted to trisubstituted by identical or different substituents selected from the group consisting of fluorine, chlorine, bromine, iodine, cyano, nitro, hydroxyl, mercapto, amino, straight-chain or branched alkyl having 1 to 4 carbon atoms, straight-chain or branched halogenalkyl having 1 to 4 carbon atoms and 1 to 9 fluorine and/or chlorine atoms, straight-chain or branched alkoxy or alkylthio each of which has 1 to 4 carbon atoms, straight-chain or branched halogenalkoxy or halogenoalkylthio each of which has 1 to 4 carbon atoms and each of which has 1 to 9 fluorine plus chlorine atoms, straight-chain or branched alkenyl or alkynyl each of which has 2 to 4 carbon atoms, straight-chain or branched alkenyloxy or alkinyloxy each of which has 3 to 4 carbon atoms, cycloalkyl having 3 to 6 carbon atoms, phenyl, phenoxy, phenylthio, phenylalkoxy or phenylalkylthio each of which has 1 or 2 carbon atoms in the alkyl moiety.

3. A pyridinylpyrimidine according to claim 1, in which $R^1$ represents hydrogen, fluorine, chlorine, methoxy, ethoxy, n-propoxy or i-propoxy, methylthio, ethylthio, trifluoromethyl, trichloromethyl, difluoromethyl or chlorofluoromethyl, or represents methylamino, dimethylamino, ethylamino, diethylamino, or represents a radical selected from

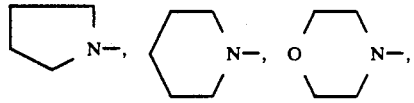

-continued

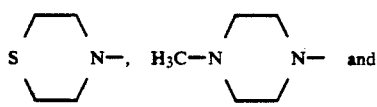

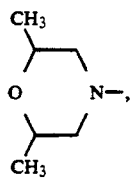

R¹ furthermore represents phenoxy, phenylthio, benzyloxy or benzylthio;

R² represents hydrogen, fluorine, chlorine, bromine, methyl, ethyl, n-proyl or i-propyl, or represents trifluoromethyl, trichloromethyl, difluoromethyl, dichloromethyl, or represents methoxy or ethoxy, or represents methylthio, or represents methoxy- or ethoxycarbonyl, R³ represents hydrogen, fluorine, chlorine, bromine, methyl, ethyl, n-propyl, i-propyl or t-butyl, R⁴ represents hydrogen, fluoroine, chlorine, bromine, methyl, trifluormethyl, trichloromethyl, hydroxyl, mercapto, methoxy, ethoxy, n-propoxy, i-propoxy, methylthio, ethylthio, n-propylthio or i-propylthio, n-butylthio, i-butylthio, s-butylthio or t-butylthio, or represents amino, methylamino, ethylamino, dimethylamino, diethylamino, or represents a radical selected from

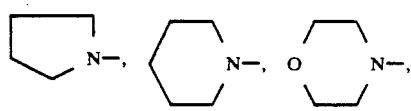

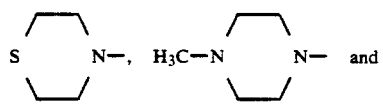

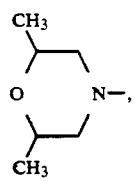

or represents 2-propenyloxy or 2-propynyloxy,

R⁵ represents hydrogen, methyl, ethyl, n-propyl, i-propyl or n-butyl and

Ar represents phenyl which is optionally monosubstituted to trisubstituted by identical or different substituents selected from the group consisting of fluorine, chlorine, bromine, iodine, cyano, nitro, hydroxyl, amino, mercapto, methyl, ethyl, n-propyl or i-propyl, n-butyl, s-butyl, i-butyl, or t-butyl, trifluoromethyl, trichloromethyl, difluoromethyl, methoxy, ethoxy, methylthio, ethylthio, trifluoromethoxy, difluoromethoxy, trifluoromethylthio, chlorodifluoromethylthio, morpholino, phenylamino, hydrazino, 2-phenylthydrazino, 2,2-dimethylhydrazino, 2-phenylhydrazine, methylcarbonylamino, phenylcarbonylamino, aminocarbonyl, methylaminocarbonyl, dimethylaminocarbonyl, methoxycarbonyl and ethoxycarbonyl.

4. A compound according to claim 1, wherein such compound is 2-(2-pyridyl)-4-(4-chloro-phenyl)-pyrimidine of the formula

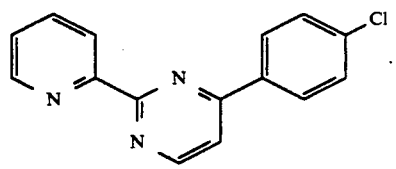

5. A compound according to claim 1, wherein such compound is 2-(2-pyridyl)-4-(4-trifluoromethylphenyl)pyrimidine of the formula

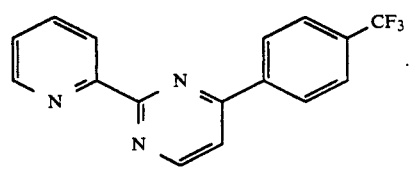

6. A compound according to claim 1, wherein such compound is 2-(2-pyridyl)-4-(4-fluoro-phenyl)-5-methylpyridmine of the formula

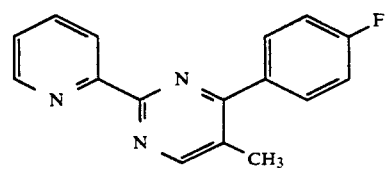

7. A compound according to claim 1, wherein such compound is 2-(2-pyridyl)-4-(2-hydroxy-phenyl)-pyrimidine of the formula

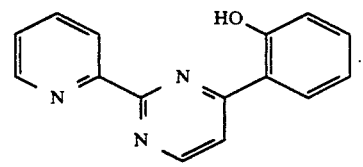

8. A compound according to claim 1, wherein such compound is 2-(2-pyridyl)-4-phenyl-6-ethylthio-pyrimidine of the formula

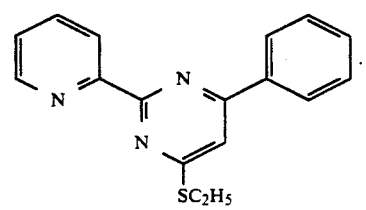

9. A compound according to claim 1, wherein such compound is 2-(2-pyridyl-4-(4-isobutyl-phenyl)-pyrimidine of the formula

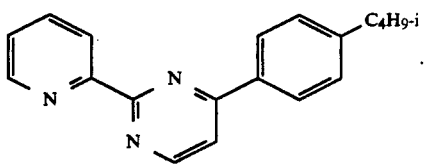

10. A compound according to claim 1, wherein such compound is 2-(2-pyridyl)-4-(2-fluoro-phenyl)-6-hydroxypyrimidine of the formula

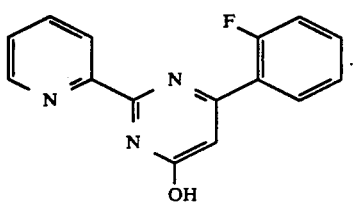

11. A fungicidal composition comprising a fungicidally effective amount of a compound according to claim 1 and a diluent.

12. A method of combating fungi which comprises applying to such fungi or to a fungus habitat a fungicidally effective amount of a compound of the formula

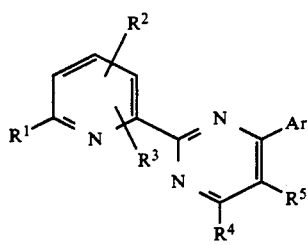

in which $R^1$ represents hydrogen, halogen, in each case straight-chain or branched alkoxy or alkylthio each of which has 1 to 6 carbon atoms, or represents straight-chain or branched halogenalkyl having 1 to 6 carbon atoms and 1 to 13 identical or different halogen atoms, amino, alkylamino or dialkylamino each of which has 1 to 6 carbon atoms in the respective straight-chain or branched alkyl moieties, or represents a radical selected from

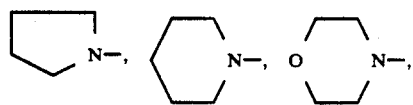

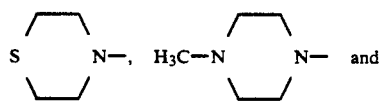

or

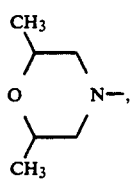

or $R^1$ furthermore represents phenoxy or phenylthio, each of which is optionally monosubstituted, disubstituted or trisubstituted by identical or different substituents selected from the group consisting of halogen, cyano, nitro, alkyl having 1 or 2 carbon atoms, alkoxy having 1 or 2 carbon atoms, alkylthio having 1 or 2 carbon atoms, halogenalkyl having 1 or 2 carbon atoms and 1 to 5 fluorine plus chlorine atoms, halogenalkoxy having 1 or 2 carbon atoms and 1 to 5 fluorine plus carbon atoms, halogenalkylthio having 1 or 2 carbon atoms, or $R^1$ represents phenylalkoxy or phenylalkylthio each of which has 1 to 4 carbon atoms in the respective straight-chain or branched alkyl moiety and each of which is optionally substituted on the phenyl moiety by identical or different substituents selected from the group consisting of halogen, cyano, nitro, alkyl, alkoxy or alkylthio each of which has 1 or 2 carbon atoms, and also halogenalkyl, halogenalkoxy or halogenoalkylthio each of which has 1 or 2 carbon atoms and each of which has 1 to 5 fluorine plus chlorine atoms, $R_2$ and $R_3$ are independent of one another and identical or different and in each case represent hydrogen, halogen, straight-chain or branched alkyl having 1 to 6 carbon atoms, or represents straight-chain or branched halogenalkyl having 1 to 6 carbon atoms and 1 to 13 identical or different halogen atoms, or represents straight-chain or branched alkoxy or alkylthio each of which has 1 to 6 carbon atoms, or represents straight-chain or branched alkoxycarbonyl having 1 to 6 carbon atoms in the alkoxy moiety, or $R^2$ and $R^3$ together represent an alkylene chain which has 3 to 5 carbon atoms and which is linked via the ring positions 3 and 4 or 4 and 5.

$R^4$ represents hydrogen; halogen; straight-chain or branched alkyl having 1 to 6 carbon atoms; straight-chain or branched halogenalkyl having 1 to 6 carbon atoms and 1 to 13 identical or different halogen atoms; hydroxyl; mercapto; straight-chain or branched alkoxy or alkylthio each of which has 1 to 6 carbon atoms; amino; alkylamino or dialkylamino each of which has 1 to 6 carbon atoms in the respective straight-chain or branched alkyl moieties; or $R^4$ represents a radical selected from

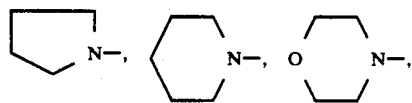

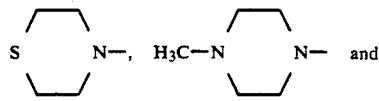

-continued

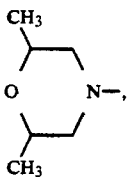

or represents in each case straight-chain or branched alkenyloxy or alkynyloxy each of which has 2 to 6 carbon atoms, R⁵ represents hydrogen or straight-chain or branched alkyl having 1 to 6 carbon atoms, and Ar represents phenyl which is optionally monosubstituted, disubstituted or trisubstituted by identical or different substituents selected from the group consisting of halogen, cyano, nitro, hydroxyl, amino, mercapto, straight-chain or branched alkyl having 1 to 6 carbon atoms, straight-chain or branched halogenoalkyl having 1 to 6 carbon atoms and 1 to 13 identical or different halogen atoms, straight-chain or branched alkoxy or alkylthio each of which has 1 to 6 carbon atoms, straight chain or branched halogenalkylthio or halogenalkoxy each of which has 1 to 6 carbon atoms and each of which has 1 to 13 identical or different halogen atoms, straight-chain or branched alkenyl or alkynyl having 2 to 6 carbon atoms, straight-chain or branched alkenyloxy or alkynyloxy having 2 to 6 carbon atoms, cycloalkyl having 3 to 8 carbon atoms, phenyl, phenoxy, phenylthio, and phenylalkylthio or phenylalkyloxy each of which has 1 to 4 carbon atoms in the straight-chain or branched alkyl moiety.

13. The method according to claim 12, wherein such compound is
2-(2-pyridyl)-4-(4-chloro-phenyl)-pyrimidine,
2-(2-pyridyl)-4-(4-trifluoromethyl-phenyl)pyrimidine,
2-(2-pyridyl)-4-(4-fluoro-phenyl)-5-methylpyrimidine,
2-(2-pyridyl)-4-(2-hydroxy-phenyl)-pyrimidine,
2-(2-pyridyl)-4-phenyl-6-ethylthio-pyrimidine,
2-(2-pyridyl)-4-(4-isobutyl-phenyl)-pyrimidine or
2-(2-pyridyl)-4-(2-fluoro-phenyl)-6-hydroxy-pyrimidine.

14. A pyridinylpyrimidine of the formula

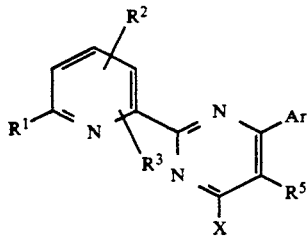

in which

R¹ represents hydrogen, halogen, in each case straight-chain or branched alkoxy or alkylthio each of which has 1 to 6 carbon atoms, or represents straight-chain or branched halogenoalkyl having 1 to 6 carbon atoms and 1 to 13 identical or different halogen atoms, or R¹ represents amino, alkylamino or dialkylamino each of which has 1 to 6 carbon atoms in the respective straight-chain or branched alkyl moieties, or R¹ represents a radical selected from

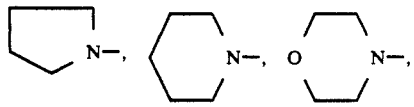

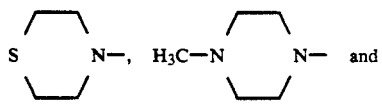

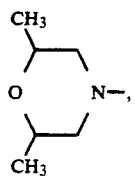

or

R¹ furthermore represents phenoxy or phenylthio, each of which is optionally monosubstituted, disubstituted or trisubstitued by identical or different substituents selected from the group consisting of halogen, cyano, nitro, alkyl, alkoxy or alkylthio each of which has 1 or 4 carbon atoms, and also halogenalkyl, halogenoalkoxy or halogenalkylthio each of which has 1 or 2 carbon atoms and each of which has 1 to 5 fluorine plus chlorine atoms, or R¹ represents phenylalkoxy or phenylalkylthio each of which has 1 to 4 carbon atoms in the respective straight-chain or branched alkyl moiety and each of which is optionally monosubstituted, disubstituted or trisubstituted on the phenyl moiety by identical or different substituents selected from the group consisting of halogen, cyano, nitro, alkyl, alkoxy or alkylthio each of which has 1 or 2 carbon atoms, and also halogenalkyl, halogenalkoxy or halogenoalkylthio each of which has 1 or 2 carbon atoms and each of which has 1 to 5 fluorine plus chlorine atoms, R² and R³ are independent of one another and identical or different and is each case represent hydrogen, halogen, straight-chain or branched alkyl having 1 to 6 carbon atoms, or represents straight-chain or branched halogenoalkyl having 1 to 6 carbon atoms and 1 to 13 identical or different halogen atoms, or represents in each case straight-chain or branched alkoxy or alkylthio each of which has 1 to 6 carbon atoms, or represents straight-chain or branched alkoxycarbonyl having 1 to 6 carbon atoms in the alkoxy moiety, or R² and R³ together represent an alkylene chain which has 3 to 5 carbon atoms and which is linked via the ring positions 3 and 4 or 4 and 5, X represents halogen, and R⁵ represents hydrogen or straight-chain or branched alkyl having 1 to 6 carbon atoms.

15. A pyridinylpyrimidine derivative of the formula

16. A pyridinylpyrimidine derivative of the formula
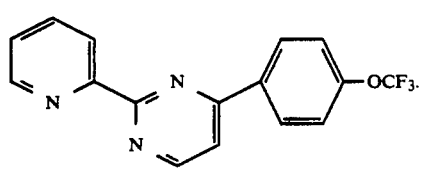
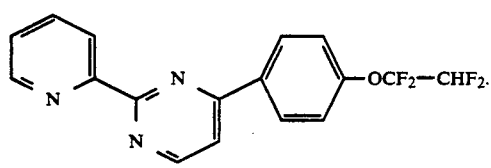
17. A pyridinylpyrimidine derivative of the formula
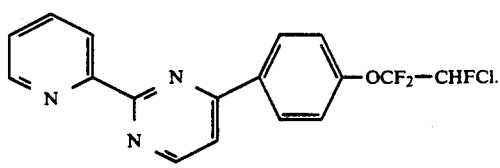
18. A pyridinylpyrimidine derivative of the formula
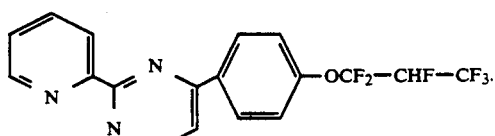
* * * * *